US010426371B2

(12) United States Patent
Watanabe et al.

(10) Patent No.: US 10,426,371 B2
(45) Date of Patent: Oct. 1, 2019

(54) MUSCLE CONDITION MEASUREMENT SHEET

(71) Applicants: Umemura Educational Institutions, Aichi (JP); SMK Corporation, Tokyo (JP)

(72) Inventors: Kohei Watanabe, Aichi (JP); Koichiro Ejiri, Kanagawa (JP); Haruhiko Kondo, Kanagawa (JP); Tsubasa Tanaka, Tokyo (JP)

(73) Assignees: SMK Corporation, Tokyo (JP); Umemura Educational Institutions, Aichi (JP)

( * ) Notice: Subject to any disclaimer, the term of this patent is extended or adjusted under 35 U.S.C. 154(b) by 262 days.

(21) Appl. No.: 15/432,947

(22) Filed: Feb. 15, 2017

(65) Prior Publication Data

US 2017/0347908 A1    Dec. 7, 2017

(30) Foreign Application Priority Data

Jun. 7, 2016 (JP) ................................ 2016-113372
Aug. 1, 2016 (JP) ................................ 2016-150949

(51) Int. Cl.
*A61B 5/0492*     (2006.01)
*A61B 5/0488*     (2006.01)
(Continued)

(52) U.S. Cl.
CPC ........ *A61B 5/0492* (2013.01); *A61B 5/04004* (2013.01); *A61B 5/0408* (2013.01);
(Continued)

(58) Field of Classification Search
CPC .... A61B 2560/0412; A61B 2560/0468; A61B 2562/0209; A61B 2562/046;
(Continued)

(56) References Cited

U.S. PATENT DOCUMENTS

| 2008/0147146 A1* | 6/2008 | Wahlgren ........... A61B 5/04001 607/61 |
| 2009/0299212 A1* | 12/2009 | Principe ............. A61B 5/04882 600/547 |

(Continued)

FOREIGN PATENT DOCUMENTS

| JP | 2001-276005 A | 10/2010 |
| JP | 2015051158 A | 3/2015 |
| JP | 2015-066401 A | 4/2015 |
| JP | 2005-144108 A | 6/2015 |

OTHER PUBLICATIONS

Bronzino, Joseph D.. (2006). Biomedical Engineering Handbook, (3rd Edition). Taylor & Francis. vol. 1, Section 19.8, Retrieved from https://app.knovel.com/hotlink/toc/id:kpBEHBEFE4/biomedical-engineering/biomedical-engineering (Year: 2006).*

(Continued)

*Primary Examiner* — David J. McCrosky

(57) ABSTRACT

An object of the present disclosure is to provide a muscle condition measurement sheet that can quantitatively detect the amplitude and latency of an evoked electromyogram EMG or an evoked mechanomyogram MMG and correctly evaluate the state of activity of a muscle. A pair of stimulating electrodes and all myoelectric detection electrodes come into intimate contact with a body surface of a muscle, appearing on a back surface of an insulating sheet spaced at predetermined intervals; accordingly, the relative position between an electrical stimulation position and the myoelectric detection electrode is fixed and the amplitude and latency of the evoked electromyogram EMG can be quantitatively detected without depending on the stimulation position of an electrical stimulation signal.

16 Claims, 16 Drawing Sheets

(51) Int. Cl.
*A61B 5/22* (2006.01)
*A61B 5/04* (2006.01)
*A61B 7/00* (2006.01)
*A61B 5/0408* (2006.01)
*A61B 5/0484* (2006.01)
*A61B 5/00* (2006.01)

(52) U.S. Cl.
CPC .......... *A61B 5/0484* (2013.01); *A61B 5/0488* (2013.01); *A61B 5/224* (2013.01); *A61B 5/7225* (2013.01); *A61B 7/006* (2013.01); *A61B 5/6831* (2013.01); *A61B 5/6832* (2013.01); *A61B 2560/0412* (2013.01); *A61B 2560/0468* (2013.01); *A61B 2562/046* (2013.01); *A61B 2562/164* (2013.01); *A61B 2562/166* (2013.01)

(58) Field of Classification Search
CPC ... A61B 5/0488; A61B 5/4519; A61B 5/6833; A61N 1/0476; A61N 1/0492; A61N 1/36014
See application file for complete search history.

(56) References Cited

U.S. PATENT DOCUMENTS

| | | | |
|---|---|---|---|
| 2012/0277834 A1* | 11/2012 | Mercanzini | A61B 5/04001 607/62 |
| 2013/0165813 A1* | 6/2013 | Chang | A61B 5/0492 600/546 |
| 2014/0235991 A1* | 8/2014 | Gadsby | A61B 5/04001 600/391 |
| 2015/0025410 A1* | 1/2015 | Wolpaw | A61N 1/36082 600/546 |
| 2015/0171321 A1* | 6/2015 | Chan | H01L 45/1253 257/4 |
| 2015/0313521 A1* | 11/2015 | Say | A61B 5/157 600/347 |

OTHER PUBLICATIONS

Office Action issued for counterpart Japanese Application No. 2016-150949, issued by the Japan Patent Office dated Dec. 18, 2018 (drafted on Nov. 20, 2018).

* cited by examiner

MUSCLE CONDITION MEASUREMENT SHEET

CROSS REFERENCE TO RELATED APPLICATION

The contents of the following Japanese patent applications are incorporated herein by reference, Japanese Patent Application No. 2016-113372 filed on Jun. 7, 2016 and Japanese Patent Application No. 2016-150949 filed on Aug. 1, 2016.

FIELD

The present disclosure relates to a muscle condition measurement sheet used in an evaluation system that evaluates the state of activity of a skeletal muscle based on a muscle action potential evoked by nerve stimulation.

BACKGROUND

A skeletal muscle generates action potentials when contracting and expanding by nerve stimulation from the brain. An evaluation system, which detects the action potentials and evaluates muscle abnormalities and levels of fatigue based on an electromyogram (electromyogram: EMG) being a waveform of the action potentials, can be developed. However, when the action potentials are detected while the skeletal muscle contracts and expands, an electrical signal resulting from stimulation from the brain and an action potential generated by the muscle during exercise are included as noise; accordingly, the state of activity of the muscle is not able to be stably evaluated.

Hence, an evaluation system has been proposed which adds an electrical stimulation signal to a skeletal muscle, detects a muscle action potential evoked by the nerve stimulation of the electrical stimulation signal from a detection electrode in intimate contact with a body surface of the skeletal muscle, and evaluates the state of activity of the muscle. When a peripheral nerve of a muscle to be evaluated is innervated by an electrical stimulation signal, excitation reaches the muscle via a motor nerve to generate, in the muscle, muscle action potentials that cause the muscle to contract. The waveform of the muscle action potentials is called the M-wave. The muscle action potentials are detected from the body surface of the muscle; accordingly, an evoked electromyogram of the M-wave can be obtained. On the other hand, when the peripheral nerve is innervated, excitation also reaches the spine via a sensory nerve. α-cells are excited via a monosynaptic reflex. Muscle action potentials that cause the muscle to contract are then generated via a motor nerve. The waveform of the muscle action potentials generated later than the M-wave is called the H-wave. In related muscle evaluation systems, the state of activity of the muscle is evaluated based on the amplitude of the M-wave or H-wave.

Of them, an evoked electromyography apparatus 3 disclosed in JP-A-2005-144108 includes a stimulation terminal fixing purpose belt 1 that brings a stimulating electrode 1-1 into intimate contact with a body surface of a site, in which the tibial nerve travels, of the popliteal fossa, a recording terminal fixing purpose belt 2 that brings a plurality of myoelectric detection electrodes 2-1, 2-1 . . . respectively into intimate contact at different positions with a body surface along the soleus of which state of activity is evaluated, a stimulation generation device 3-1 that outputs an electrical stimulation signal to the stimulating electrode 1-1, a recording device 3-2 that records muscle action potentials detected by the myoelectric detection electrodes 2-1, 2-1 . . . , and a processing device 3-3 that evaluates the state of activity of the soleus from an evoked electromyogram, as illustrated in FIG. 15.

In the evoked electromyography apparatus 100, an electrical stimulation signal is output to the stimulating electrode 101 to detect the amplitude of the H-wave from the myoelectric detection electrodes 103, 103 . . . . The amplitude of the H-wave represents the amount of activity of the muscle being the amount of stimulation from the spinal motor neurons for the soleus. Accordingly, the amplitudes of the H-wave detected at rest and during exercise are compared to evaluate the state of activity of the soleus.

Moreover, an apparatus for evaluating the level of activity of a muscle, the apparatus being disclosed in JP-A-2001-276005, measures an evoked electromyogram of the M-wave from myoelectric detection electrodes in intimate contact with a body surface along the direction of the muscle fibers in addition to a body surface of a muscle where an electrical stimulation signal is measured, and evaluates the activity level and fatigue level of the muscle from the amplitude of the M-wave.

Furthermore, a method for assisting in determining the presence or absence of a disorder of excitation-contraction coupling, the method being disclosed in JP-A-2015-66401, adds an electrical stimulation signal to evaluate a disorder of muscle in combination with an evoked electromyogram EMG detected from a body surface and an evoked mechanomyogram (mechanomyogram: MMG) evoked by the electrical stimulation signal. The evoked mechanomyogram MMG is a vibration waveform obtained by recording a mechanical variable in a major axis direction of the muscle involved with contraction induced by electrical stimulation. The evoked mechanomyogram MMG is considered as a kind of pressure wave that vibrates in a frequency band equal to or less than 100 Hz that is smaller by one order of magnitude than the frequency band of the evoked electromyogram EMG. In JP-A-2015-66401, a myoelectric detection electrode and an accelerometer are fixed onto a body surface of a muscle to be measured, and onto a body surface of the belly of the muscle where the amplitude of the muscle is at its maximum, respectively, with adhesive tape. A single electrical stimulation signal of 1 Hz is added to a body surface near the muscle to detect the evoked electromyogram EMG from the myoelectric detection electrode and detect the evoked mechanomyogram MMG from the accelerometer.

The difference in distal latency between the detected evoked electromyogram EMG and evoked mechanomyogram MMG is obtained. If the difference in distal latency is increased as compared to one under normal conditions, or if the amplitude of the evoked mechanomyogram MMG dwindles although the amplitude of the evoked electromyogram EMG is constant, it is evaluated as having a disorder of excitation-contraction coupling. According to the invention of JP-A-2015-66401, the evoked electromyogram EMG and the evoked mechanomyogram MMG are used in combination; accordingly, it is possible to determine a disorder of excitation-contraction coupling correctly and excellently in reproducibility.

As described above, the state of activity of a muscle can be evaluated based on the amplitude of the evoked electromyogram EMG and the difference in distal latency between the evoked electromyogram EMG and the evoked mechanomyogram MMG. However, the amplitude of the evoked electromyogram EMG and the distal latencies of the evoked electromyogram EMG and the evoked mechanomyogram MMG vary according to the stimulation position to which an electrical stimulation signal is applied and the distance between the stimulation position and the myoelectric detection electrode or the accelerometer that detects evoked muscle sound.

However, in any evaluation system described in JP-A-2005-144108, JP-A-2001-276005, and JP-A-2015-66401, the stimulation position to which an electrical stimulation signal for a muscle to be evaluated is applied is not clear, and the myoelectric detection electrode and the accelerometer that detects evoked muscle sound are not brought into intimate contact with the body surface, at the positions predetermined distances away from the stimulation position. Accordingly, it is not possible to quantitatively detect the amplitude and distal latency of the evoked electromyogram EMG or the evoked mechanomyogram MMG and correctly evaluate the state of activity of the muscle.

Especially in the evaluation system of JP-A-2015-66401, an electrical stimulation signal cannot be applied to a fixed position during exercise. Accordingly, it is not possible to evaluate a load and the state of activity of the muscle while a load is applied to the muscle; therefore, it is not possible to observe secular changes in the state of activity of the muscle in real time during exercise.

Moreover, the inventor of the present application has found that when muscle fatigue increases due to exercise, the propagation speed of the M-wave caused by an electrical stimulation signal reduces, and there is a correlation between muscle fatigue and the propagation speed. However, the propagation speed of the M-wave is obtained based on the time (latency) between when the electrical stimulation signal is applied to when the myoelectric detection electrode detects the M-wave, and the interval between the stimulation position and the myoelectric detection electrode or between the myoelectric detection electrodes. Accordingly, in the related evaluation systems where these intervals are unknown cannot evaluate the level of fatigue of a muscle caused by exercise based on the propagation speed of the M-wave.

Furthermore, a muscle to be measured is under the body surface. Accordingly, the myoelectric detection electrode cannot be brought into intimate contact with the body surface at a position along the muscle fibers; hence, a correct evoked electromyogram cannot be obtained.

The present disclosure has been made considering such problems, and an object thereof is to provide a muscle condition measurement sheet that can quantitatively detect the amplitude and latency of an evoked electromyogram EMG or an evoked mechanomyogram MMG and correctly evaluate the state of activity of a muscle.

Moreover, another object is to provide a muscle condition measurement sheet that can evaluate the state of activity of a muscle in real time even during an exercise where a load is applied to the muscle.

Another object is to provide a muscle condition measurement sheet that evaluates the level of fatigue of a muscle based on a latency of a myoelectric detection electrode in detection.

SUMMARY

In order to achieve the above objects, a muscle condition measurement sheet according to a first aspect is a muscle condition measurement sheet used in an evaluation system for positioning a back surface of an insulating sheet on a body surface of a muscle to be measured, the back surface being on a side facing the body surface, applying an electrical stimulation signal to a body surface near the muscle to be measured, and evaluating the state of activity of the muscle based on muscle action potentials appearing on the body surface near the muscle, the muscle condition measurement sheet including: a pair of stimulating electrodes including an anode and a cathode between which an electrical stimulation signal is output; one or two or more myoelectric detection electrodes configured to detect a muscle action potential evoked by the electrical stimulation signal; an insulating sheet causing the pair of stimulating electrodes and the one or two or more myoelectric detection electrodes to appear on a back surface thereof such that an interval between the stimulating electrode and at least any of the myoelectric detection electrodes, which are exposed from the back surface, is shorter than the length of a muscle fiber of the muscle to be measured; and lead patterns wired on the insulating sheet to extend the pair of stimulating electrodes and all the myoelectric detection electrodes respectively to external circuits, wherein the pair of stimulating electrodes and all the myoelectric detection electrodes are brought into intimate contact with a body surface, spaced at predetermined intervals.

The pair of stimulating electrodes and all the myoelectric detection electrodes come into intimate contact with the body surface, spaced at predetermined intervals. Accordingly, the interval between any of the myoelectric detection electrodes and the pair of stimulating electrodes and the interval between any of the myoelectric detection electrodes and the other myoelectric detection electrode are measurable fixed intervals, respectively. The amplitude and latency of the evoked electromyogram EMG can be quantitatively detected without depending on the stimulation position of the electrical stimulation signal.

Moreover, the pair of stimulating electrodes and the one or two or more myoelectric detection electrodes are caused to appear on the back surface of the insulating sheet such that the interval between the stimulating electrodes and at least any of the myoelectric detection electrodes is made shorter than the length of the muscle fiber of the muscle to be measured. Accordingly, it is ensured to innervate the muscle with the electrical stimulation signal and detect muscle action potentials that propagate through the muscle after the stimulation with the myoelectric detection electrodes without the stimulating electrodes and any of the myoelectric detection electrodes deviating from the body surface of the muscle to be measured.

Since the insulating sheet is positioned on the body surface of the muscle to allow the pair of stimulating electrodes and the myoelectric detection electrodes to come into intimate contact with the body surface, even if they vibrate, they do not come off the body surface and can detect secular changes in the evoked electromyogram EMG at the same positions in real time even during exercise.

In the muscle condition measurement sheet according to a second aspect, a reference electrode having a constant potential appears on the back surface of the insulating sheet, and the muscle action potential of the myoelectric detection electrode is detected based on a difference in potential from the reference electrode in intimate contact with the body surface.

The muscle action potential is detected based on a difference between the potential of the reference electrode having a constant potential and the potential of the myoelectric detection electrode.

In the muscle condition measurement sheet according to a third aspect, the insulating sheet is a long and slim band-shaped sheet body to be positioned on the body surface along the muscle to be measured, the pair of stimulating electrodes is caused to appear at one end in a longitudinal direction of the back surface of the sheet body, and the plurality of myoelectric detection electrodes is caused to appear respectively at different positions along the longitudinal direction from the one end toward the other end of the back surface of the sheet body.

The insulating sheet is a long and slim band-shaped sheet body. Accordingly, the insulating sheet is positioned along the body surface of the muscle to be measured to bring the pair of stimulating electrodes at the one end and the plurality of myoelectric detection electrodes from the one end toward the other end into intimate contact with the body surface at the different positions along the long and slim muscle fibers of the muscle to be measured even during an exercise to contract and expand the muscle.

The M-wave of the muscle action potentials evoked by the electrical stimulation signal propagates along the direction of the muscle fibers of the muscle to be measured, and is detected by each of the plurality of myoelectric detection electrodes in intimate contact with the body surface at the different positions along the muscle fibers. The mutual intervals between the pair of stimulating electrodes and the plurality of myoelectric detection electrodes are known. Accordingly, the propagation speed of the M-wave can be detected in real time based on the latencies detected by the myoelectric detection electrodes even during exercise.

In the muscle condition measurement sheet according to a fourth aspect, the pair of stimulating electrodes and the plurality of myoelectric detection electrodes are caused to appear respectively at positions distributed on a flat surface of the back surface of the insulating sheet.

Even if the insulating sheet is not positioned on the body surface along the muscle to be measured, any of the myoelectric detection electrodes appearing at the positions distributed on the flat surface appears in the vicinity along the muscle to be measured. Accordingly, the propagation speed of the M-wave along the muscle is detected based on the latency detected by the myoelectric detection electrode.

Even if the muscle to be measured has a spindle shape that is thick in the middle in the muscle fiber direction and is thin at both ends, the plurality of myoelectric detection electrodes comes into intimate contact at positions on the body surface of the spindle-shaped muscle. Accordingly, any of the myoelectric detection electrodes detect the propagating M-wave at different positions of the muscle.

The body surface of the muscle to be measured has a curved surface curving outward in the middle of the muscle. However, any of the myoelectric detection electrodes appearing at the positions distributed on the flat surface come into intimate contact with the body surface to detect the M-wave at a high detection level.

In the muscle condition measurement sheet according to a fifth aspect, the pair of stimulating electrodes is caused to appear at one end of the back surface of the insulating sheet, and the plurality of myoelectric detection electrodes is caused to appear respectively at positions distributed in a grid pattern on the back surface of the insulating sheet.

The plurality of myoelectric detection electrodes appears at the positions distributed in a grid pattern. Accordingly, any of the plurality of myoelectric detection electrodes appearing at the positions on straight lines is in close proximity to the muscle fiber direction of the muscle to be measured. Accordingly, the propagation speed of the M-wave that propagates along the muscle fiber direction can be obtained based on the latency of the M-wave detected by the myoelectric detection electrodes in close proximity to the muscle fiber direction.

In the muscle condition measurement sheet according to a sixth aspect, a position where one of the stimulating electrodes, the anode or the cathode, appears on the back surface of the insulating sheet is centered, and the other stimulating electrode is caused to appear in a ring form at a position around the center, and the plurality of myoelectric detection electrodes is caused to appear respectively at positions distributed on a plurality of circles being concentric around the center.

The position where one of the pair of stimulating electrodes appears is centered, and the plurality of myoelectric detection electrodes appears distributed respectively at the positions on the plurality of circles being concentric around the center. Accordingly, any of the plurality of myoelectric detection electrodes on the concentric circles centered on the stimulating electrode is located substantially parallel to the direction of the muscle fibers of the muscle to be evaluated. The myoelectric detection electrodes detect the muscle action potential evoked by the electrical stimulation signal.

Moreover, the plurality of myoelectric detection electrodes appears distributed at the positions on the concentric circles centered on the stimulation position by the electrical stimulation signal. Accordingly, the distances of a plurality of myoelectric detection electrodes appearing on the same circle to the stimulation position are equal. The latencies of the M-wave detected by the plurality of myoelectric detection electrodes appearing on the same circle are compared; accordingly, the states of activity of the muscle within the body surface where the myoelectric detection electrodes come into intimate contact can be compared.

In the muscle condition measurement sheet according to a seventh aspect, the electrical stimulation signal is equal to or greater than 5 mA, and an exposure area of at least one of the stimulating electrodes exposed from the back surface of the insulating sheet is equal to or greater than 100 mm$^2$.

The exposure area is set to equal to or greater than 100 mm$^2$; accordingly, a current value per unit area of the electrical stimulation signal applied to the body surface is reduced so that stimulation hardly causes pain.

In the muscle condition measurement sheet according to an eighth aspect, the pair of stimulating electrodes is caused to appear on the back surface, protruding from the back surface of the insulating sheet.

The stimulating electrodes press the body surface in a state where the insulating sheet is positioned on the body surface. Accordingly, even if receiving an external force such as a vibration, the stimulating electrodes maintain the state of being in intimate contact with the body surface.

In the muscle condition measurement sheet according to a ninth aspect, the muscle condition measurement sheet is used in an evaluation system for obtaining the propagation speed of a muscle action potential evoked by the electrical stimulation signal, based on latencies of the one or two or more myoelectric detection electrodes in the detection of the muscle action potential, and evaluating the state of activity of the muscle based on the propagation speed.

The interval between the pair of stimulating electrodes and each myoelectric detection electrode and the interval between the myoelectric detection electrodes are measurable distances. The propagation speed of the M-wave representing the muscle action potentials can be obtained based on the latency detected by the myoelectric detection electrode. The propagation speed of the M-wave is reduced with increasing fatigue of the muscle. Accordingly, the level of fatigue of the muscle can be quantitatively evaluated based on the propagation speed of the M-wave.

In the muscle condition measurement sheet according to a tenth aspect, an interval between the plurality of myoelectric detection electrodes appearing on the back surface of the insulating sheet along the muscle to be measured is less than 15 mm.

The propagation speed of the M-wave is equal to or greater than at least 3 m/s. The center frequency of the muscle action potential is 350 Hz at the maximum. Accordingly, the wavelength of the M-wave that propagates is equal to or greater than 8.571 mm. In terms of this wavelength, the wavelength is equal to or greater than 15 mm at equal to or less than 200 Hz being the center frequency of a normal muscle action potential. When the intervals between the plurality of myoelectric detection electrodes along the muscle to be measured are set to be less than 15 mm, the propagation speed of the M-wave can be obtained based on the difference between the latencies detected by the plurality of myoelectric detection electrodes.

In the muscle condition measurement sheet according to an eleventh aspect, each lead pattern connected to a corresponding myoelectric detection electrode thereof is formed in a shape with a cross-sectional area thereof increased in proportion to the length of the lead pattern.

Even if the plurality of myoelectric detection electrodes is placed at the different positions on the insulating sheet, and the length of each lead pattern is different, a muscle action potential detected is output via the lead pattern having the same resistance value.

In the muscle condition measurement sheet according to a twelfth aspect, the periphery of the lead pattern is surrounded by a ground conductor, spaced with an insulating interval.

The lead pattern is shielded by the ground conductor from the outside; accordingly, the muscle action potential detected by the myoelectric detection electrode is output via the lead pattern without noise from the outside being superimposed thereon.

The muscle condition measurement sheet according to a thirteenth aspect, further includes a mechanomyography sensor configured to detect micro vibration of the muscle induced by the electrical stimulation signal, wherein the insulating sheet includes the mechanomyography sensor having a detection surface appearing at a position, which does not interfere with the stimulating electrodes and the myoelectric detection electrodes, on the back surface, and the detection surface of the mechanomyography sensor is brought into intimate contact with the body surface at a predetermined distance away from the pair of stimulating electrodes.

When the pair of stimulating electrodes applies the electrical stimulation signal to the body surface of the muscle to be measured, the muscle micro-vibrates sideward orthogonal to its muscle fiber direction to generate a kind of pressure wave. The mechanomyography sensor detects the wave of vibration as an evoked mechanomyogram MMG. The interval between the detection surface of the mechanomyography sensor and the stimulation position by the pair of stimulating electrodes is fixed; therefore, the mechanomyography sensor detects the amplitude and latency of the mechanomyogram MMG quantitatively.

The detection surface of the mechanomyography sensor comes into intimate contact with the body surface; accordingly, the evoked mechanomyogram MMG evoked by electrical stimulation can be detected in real time even during the exercise to contract and expand the muscle.

The amplitude of the micro vibration is reduced with increasing fatigue of the muscle; accordingly, the level of fatigue of the muscle can be evaluated based on the amplitude of the evoked mechanomyogram MMG.

In the muscle condition measurement sheet according to a fourteenth aspect, the pair of stimulating electrodes is caused to appear in a ring form on both sides across the detection surface of the mechanomyography sensor on the back surface of the insulating sheet, and the back surface of the insulating sheet is positioned on the body surface in such a manner as to bring the detection surface of the mechanomyography sensor into intimate contact with the body surface having a maximum lateral displacement orthogonal to a muscle fiber direction of the muscle to be measured.

The detection surface of the mechanomyography sensor appears between the pair of stimulating electrodes on the back surface of the insulating sheet. Accordingly, the detection surface comes into intimate contact with the body surface of the electrical stimulation position. Moreover, the contact position is a position having a maximum lateral displacement orthogonal to the muscle fiber direction of the muscle to be measured. Accordingly, the evoked mechanomyogram MMG produced based on the micro vibration of the maximum amplitude is detected.

In the muscle condition measurement sheet according to a fifteenth aspect, the mechanomyography sensor is a microphone.

The pressure wave generated by the micro vibration of the muscle is converted by the microphone into an electrical signal to be detected.

According to the first aspect of the present invention, any myoelectric detection electrodes can securely detect the evoked electromyogram EMG evoked by the electrical stimulation signal. The amplitude and latency of the evoked electromyogram EMG do not change according to the stimulation position of the electrical stimulation signal. Accordingly, the state of activity such as the state of fatigue of the muscle and an increase/decrease in the rate of recruitment can be correctly detected.

Moreover, the state of activity of the muscle can be evaluated in real time even during the exercise to contract and expand the muscle.

Moreover, the myoelectric detection electrode that comes into intimate contact with the body surface at the position, a relative position of the myoelectric detection electrode to the stimulation position to which the electrical stimulation signal is applied being identified, can detect the evoked electromyogram EMG. Accordingly, the propagation direction and propagation speed of the muscle action potential in accordance with the type of muscle and the content of activity can be detected.

According to the second aspect of the present invention, the muscle action potential can be detected by the myoelectric detection electrode without being influenced by common-mode noise.

According to the third aspect of the present invention, the long and slim band-shaped sheet body can be positioned along the propagation direction of the muscle action potential evoked.

Moreover, the propagation speed of the muscle action potential evoked by the electrical stimulation signal can be detected in real time during the exercise to contract and expand the muscle to be measured. Accordingly, a change in the level of fatigue of the muscle to be measured can be detected based on the propagation speed of the muscle action potential that is continuously detected.

According to the fourth aspect of the present invention, even if the insulating sheet is not positioned on the body surface along the muscle to be measured, the propagation speed of the muscle action potential that propagates along the muscle can be detected.

Even if the muscle to be measured has a spindle shape that is thick in the middle in the muscle fiber direction and is thin at both ends, the plurality of myoelectric detection electrodes comes into intimate contact at the positions with the body surface of the spindle-shaped muscle. Accordingly, the propagating muscle action potential can be detected at different positions of the muscle.

Even if the body surface of the muscle to be measured has a curved surface curving outward in the middle of the muscle, any myoelectric detection electrode detects the muscle action potential at a high detection level in intimate contact with the body surface. Accordingly, the propagation speed and amplitude of the muscle action potential can be securely detected.

According to the fifth aspect of the present invention, the myoelectric detection electrode in intimate contact with the body surface along the muscle fiber direction of the muscle to be measured can be readily distinguished. The level and latency of the muscle action potential can be detected with accuracy based on this myoelectric detection electrode.

According to the sixth aspect of the present invention, any myoelectric detection electrode comes into intimate contact with the body surface near the muscle to be measured. Accordingly, the level and latency of the muscle action potential can be detected with accuracy based on this myoelectric detection electrode.

Furthermore, according to the sixth aspect of the present invention, the distance of the myoelectric detection electrodes appearing distributed at the positions on the concentric circle to the stimulation position by the electrical stimulation signal is represented as the radius of the circle. Accordingly, the propagation speed of the muscle action potential can be readily detected based on the latency in the detection of the evoked muscle action potential.

Furthermore, according to the sixth aspect of the present invention, the latencies of the M-wave detected by the plurality of myoelectric detection electrodes appearing distributed at the positions on the same circle are compared; accordingly the states of activity of the muscle within the body surface around the electrical stimulation position can be compared.

According to the seventh aspect of the present invention, even if the electrical stimulation signal is applied to the body surface, a subject does not feel discomfort.

According to the eighth aspect of the present invention, even if the stimulating electrode vibrates due to exercise or the like, the stimulating electrode can securely apply an electrical stimulation signal to the body surface in intimate contact with the body surface.

According to the ninth aspect of the present invention, the level of fatigue of the muscle can be quantitatively evaluated based on the latency detected by the myoelectric detection electrode.

According to the tenth aspect of the present invention, the propagation speed of the muscle action potential can be securely detected based on the difference between the latencies detected by the plurality of myoelectric detection electrodes.

According to the eleventh aspect of the present invention, even if the plurality of myoelectric detection electrodes is placed at the different positions on the insulating sheet and the length of each lead pattern is different, the muscle action potential detected is output via the lead pattern having the same resistance value; therefore, there is no influence of an error due to the different lengths of the lead patterns.

According to the twelfth aspect of the present invention, the muscle action potential as small as several mV on the back surface of the insulating sheet can be output via the lead pattern without receiving the influence of noise.

According to the thirteenth aspect of the present invention, the amplitude and latency of the evoked mechanomyogram MMG do not change depending on the electrical stimulation position. The state of activity of the muscle can be evaluated based on the amplitude and latency of the evoked mechanomyogram MMG.

Moreover, the state of activity of the muscle can be evaluated based on the evoked mechanomyogram MMG detected in real time even during the exercise to contract and expand the muscle.

Moreover, the level of fatigue of the muscle can be more correctly detected based on the amplitude of the evoked mechanomyogram MMG in combination with the latency detected by the myoelectric detection electrode.

According to the fourteenth aspect of the present invention, the detection surface of the mechanomyography sensor is brought into intimate contact with the body surface at the position where the amplitude of a micro vibration reaches its maximum when the electrical stimulation signal is applied; accordingly, the amplitude and vibration frequency of the evoked mechanomyogram MMG can be securely detected.

According to the fifteenth aspect of the present invention, an accelerometer is not used to detect evoked muscle sound. Accordingly, the evoked mechanomyogram MMG can be correctly detected even during exercise without including acceleration generated by a body movement as an error.

DESCRIPTION OF EMBODIMENTS

Figure 1:
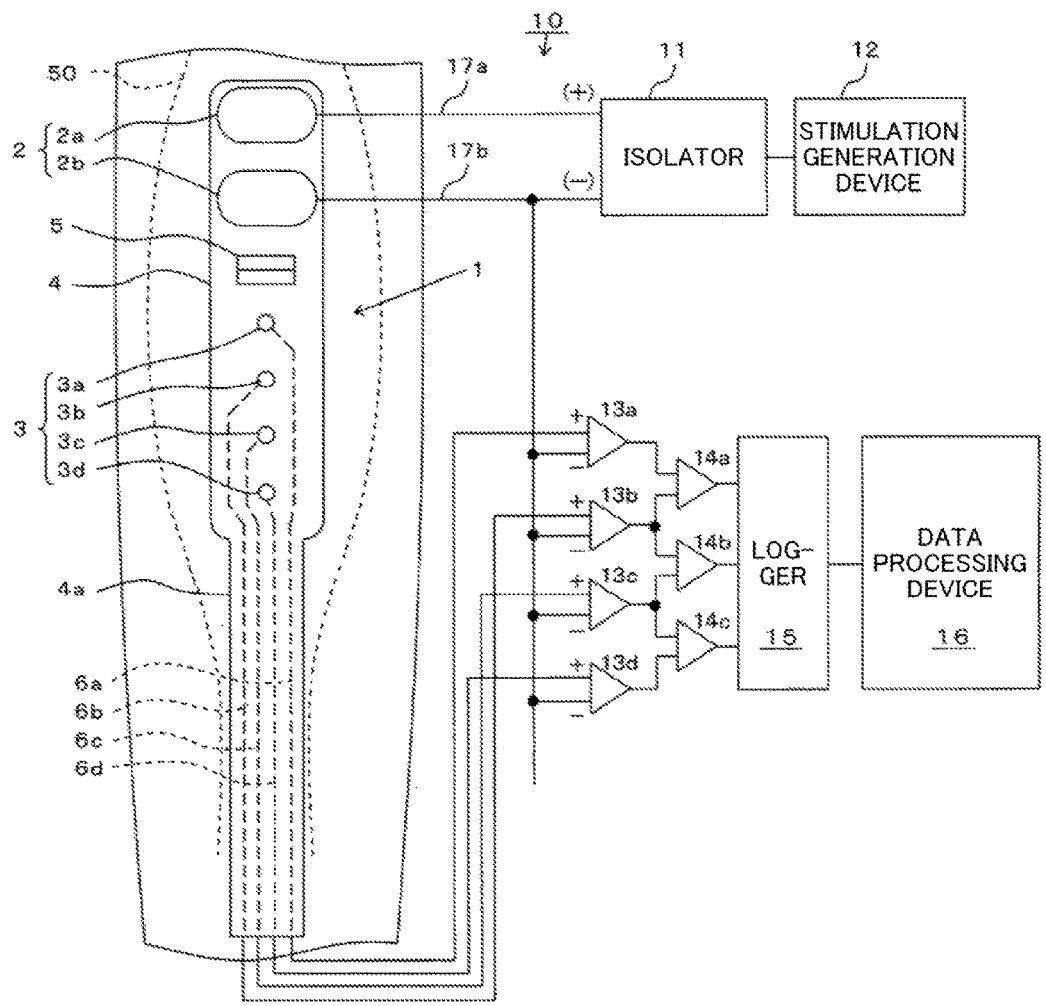
FIG. 1 is a block diagram of an evaluation system 10 that uses a muscle condition measurement sheet 1 according to a first embodiment of the invention of the present application.

As illustrated in FIG. 1, a muscle condition measurement sheet 1 according to a first embodiment of the present invention is used by an evaluation system 10 that applies an electrical stimulation signal to a muscle 50 to detect the propagation speed of a muscle action potential propagating along the muscle fiber of the muscle 50 from the stimulation position, and evaluates the level of fatigue of the muscle 50 based on the propagation speed. In order to evaluate the muscle 50, the evaluation system 10 includes a stimulation generation device 12 that outputs an electrical stimulation signal, which is described below, between a pair of stimulating electrodes 2, an anode 2a and a cathode 2b, of the muscle condition measurement sheet 1 via an isolator 11, four comparison circuits 13a, 13b, 13c, and 13d that compare potentials of four myoelectric detection electrodes 3a, 3b, 3c, and 3d of the muscle condition measurement sheet 1 with a ground potential of the cathode 2b also serving as a reference electrode to output the muscle action potentials detected by the myoelectric detection electrodes 3a, 3b, 3c, and 3d, three comparison circuits 14a, 14b, and 14c that output, to a logger 15, differences between the muscle action potentials detected by adjacent pairs of the myoelectric detection electrodes 3a, 3b, 3c, and 3d (V3a-V3b, V3b-V3c, and V3c-V3d), the logger 15 that records the differences of the muscle action potentials output from the comparison circuits 14 (V3a-V3b, V3b-V3c, and V3c-V3d) together with elapsed time, and a data processing device 16 that evaluates the level of fatigue of the muscle 50 based on the results recorded in the logger 50.

Figure 2:
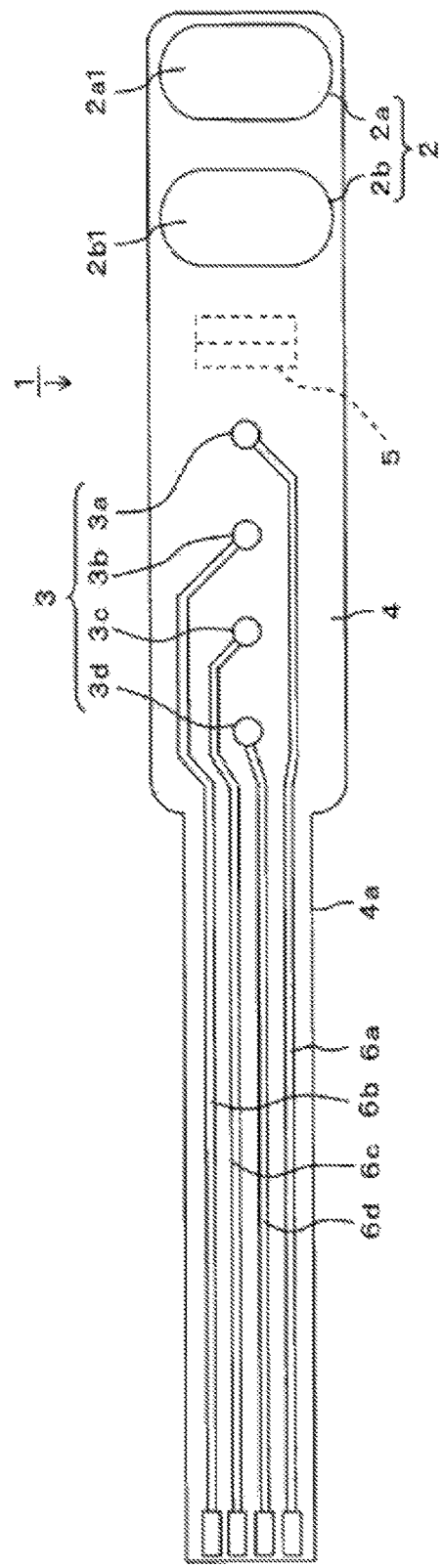
FIG. 2 is a bottom view of the muscle condition measurement sheet 1.
Figure 3:
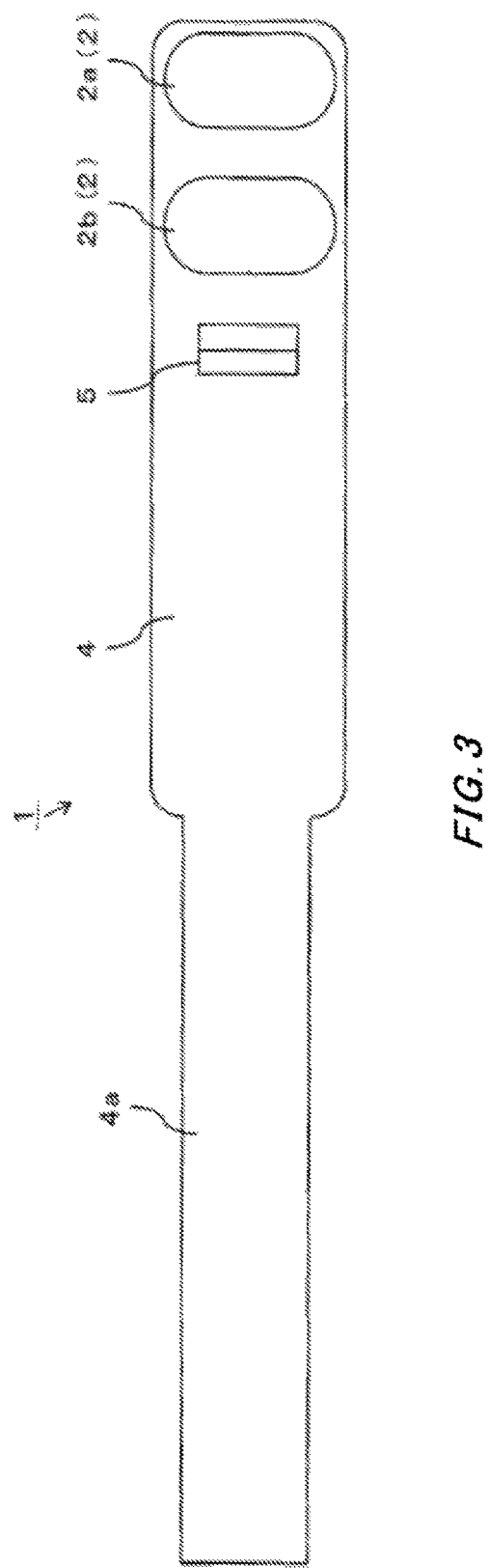
FIG. 3 is a plan view of the muscle condition measurement sheet 1.
Figure 4:
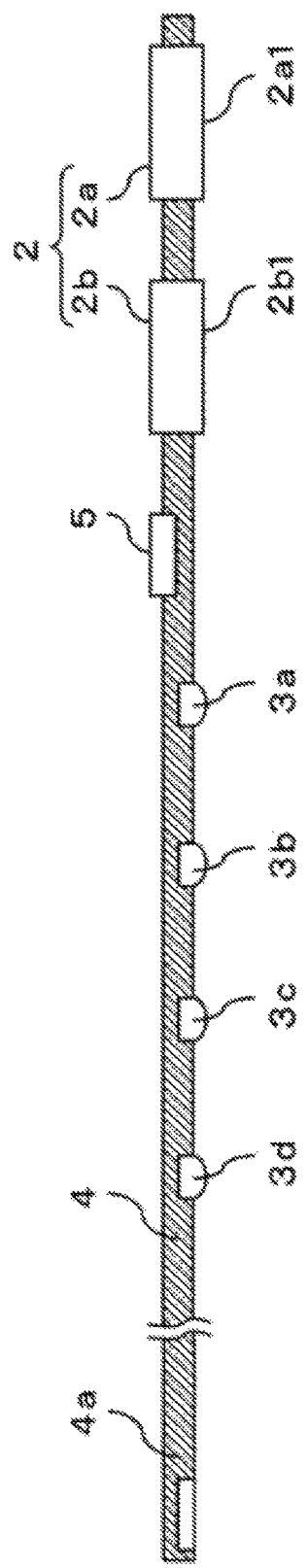
FIG. 4 is a vertical cross-sectional view of the muscle condition measurement sheet 1 cut along its longitudinal direction.

The muscle condition measurement sheet 1 is formed of a flexible print circuit (FPC) having an outside shape of a long and slim band-shape in order to be positioned on a body surface along a muscle fiber direction of the muscle fibers of the muscle 50 of which state of activity is evaluated. As illustrated in FIGS. 2 to 4, the pair of stimulating electrodes 2a and 2b, a ground electrode 5, the four myoelectric detection electrodes 3a, 3b, 3c, and 3d, four lead patterns 6a, 6b, 6c, and 6d that extend their corresponding myoelectric detection electrodes 3 to the outside are insulated from each other and formed integrally with a flexible insulating sheet body 4 made of PET or the like. Unillustrated double-sided tape is attached to substantially all over a bottom surface being a back surface, which faces the body surface, of the insulating sheet body 4 except the sites where the pair of stimulating electrodes 2a and 2b, the myoelectric detection electrodes 3a, 3b, 3c, and 3d, and external connection terminals of the lead patterns 6a, 6b, 6c, and 6d, which are described below, are exposed. Release paper of the double-sided tape is peeled off, and an adhesive layer appears. The adhesive layer is adhered to the body surface along the muscle 50 of which state of activity is evaluated to position the muscle condition measurement sheet 1. The muscle condition measurement sheet 1 is positioned on the body surface to bring the pair of stimulating electrodes 2a and 2b and the myoelectric detection electrodes 3a, 3b, 3c, and 3d into intimate contact with the body surface that the pair of stimulating electrodes 2a and 2b and the myoelectric detection electrodes 3a, 3b, 3c, and 3d face.

The pair of stimulating electrodes, the anode 2a and the cathode 2b, each have an oval-shaped outline, and are integrally formed, penetrating in a thickness direction of the insulating sheet body 4. Contact surfaces 2a1 and 2b1 on a bottom side that comes into contact with the body surface appear, slightly protruding from the bottom surface of the insulating sheet body 4, as illustrated in FIG. 4. Consequently, when the muscle condition measurement sheet 1 is positioned on the body surface, the anode 2a and the cathode 2b press the body surface, and accordingly securely come into intimate contact with the body surface at a predetermined contact pressure. Moreover, the contact surfaces 2a1 and 2b1 are covered with a gold coating to reduce the surface resistance when the anode 2a and the cathode 2b come into contact with the body surface.

The size of the contact surface 2a1 or 2b1 having an oval-shaped outline and appearing on the bottom surface of the insulating sheet body 4 is set to a size of a fixed area or more according to the current value of the electrical stimulation signal to be applied between the anode 2a and the cathode 2b. The current value of the electrical stimulation signal per unit area is set to a current value of a degree that does not cause pain due to stimulation. In the embodiment, the current value of the electrical stimulation signal is equal to or greater than 5 mA. Accordingly, the area of each of the contact surfaces 2a1 and 2b1 is set to be a size of at least 100 mm$^2$ or more.

The pair of stimulating electrodes, the anode 2a and the cathode 2b, is formed at one end of the long and slim band-shaped insulating sheet body 4 in its longitudinal direction (on the right end side in FIGS. 2 to 4). The abode 2a is placed on an outer side and the cathode 2b is placed inward of the anode 2a. When an electrical stimulation signal is flown between the anode 2a and the cathode 2b, which are in intimate contact with the body surface of the muscle 50, the electrical stimulation signal flows through the anode 2a inward, a nerve fiber in the longitudinal direction, and the cathode 2b outward during the passage of the electrical stimulation signal. The outward current causes excitation. Accordingly, a muscle action potential is generally generated around the cathode 2b at the onset of the passage of current, and a muscle action potential is generated around the anode 2a afterward. However, the electrical stimulation signal is stimulation for a short period of 0.5 msec as described below. Accordingly, it is considered that only the cathode 2b at the onset of the passage of current has the stimulation effect, and a muscle action potential evoked by stimulation is generated around the cathode 2b. Hence, when the muscle condition measurement sheet 1 is positioned along the body surface of the muscle 50 of which state of activity is evaluated, the cathode 2b of the pair of stimulating electrodes is placed inward of the anode 2a to more securely bring the cathode 2b and the myoelectric detection electrodes 3a, 3b, 3c, and 3d into intimate contact with the body surface of the muscle 50.

The anode 2a of the pair of stimulating electrodes is connected to a positive output of the isolator 11 via an electric wire 17a soldered and connected to a surface exposed on a flat surface side of the insulating sheet body 4. Moreover, the cathode 2b is connected to a negative output of the isolator 11 set to a constant potential, here, a ground potential, and inverting inputs of the comparison circuits 13a, 13b, 13c, and 13d via an electric wire 17b soldered and connected to the surface exposed on the flat surface side of the insulating sheet body 4. The cathode 2b also serves as a reference electrode to compare the ground potential with the potentials of the myoelectric detection electrodes 3a, 3b, 3c, and 3d.

The pair of stimulating electrodes 2a and 2b apply electrical stimulation to the muscle 50 of which state of activity is evaluated at regular intervals. Accordingly, even if a muscle action potential is detected while a load is being applied to the muscle, for example, during exercise, a muscle action potential evoked by electrical stimulation can be detected distinguished from an unstable muscle action potential generated when the muscle is contracted and expanded by nerve stimulation from the brain. Moreover, the anode 2a and the cathode 2b of the pair of stimulating electrodes are formed integrally with the insulating sheet body 4 of the muscle condition measurement sheet 1 positioned on the body surface of the muscle 50 to be measured. Accordingly, the electrical stimulation position is not displaced even during exercise, and the propagation speed and propagation direction of the muscle action potential can be correctly detected in real time.

The electrical stimulation signal output between the pair of stimulating electrodes 2a and 2b from the stimulation generation device 12 is a square wave having a maximum current value of 10 mA, a pulse width of 0.5 msec, and a voltage of 50 V to 100 V. The electrical stimulation signal is output between the stimulating electrodes 2a and 2b at intervals of one second. The electrical stimulation signal is set to be a square wave having a large change rate. Accordingly, it is possible to innervate a nerve fiber even at a low current value with a higher stimulation effect than an increasing stimulation waveform that increases gradually. Moreover, a single square-wave stimulation is applied at intervals of one second to facilitate the detection of the propagation speed of a muscle action potential propagating along the muscle 50.

In terms of the above-mentioned electrical stimulation signal output between the pair of stimulating electrodes 2a and 2b, it is also possible to use the electrical stimulation signal output between the pair of stimulating electrodes 2a and 2b for the purpose of training the muscle 50 by applying electrical stimulation to the muscle 50 and contracting and expanding the muscle 50. For example, an electrical stimulation signal of a frequency in the neighborhood of 20 Hz is suitable for the electrical stimulation signal output from the stimulation generation device 12 for the purpose of training the muscle 50. A muscle action potential evoked by outputting this electrical stimulation signal may be detected at the myoelectric detection electrodes 3a, 3b, 3c, and 3d. Moreover, it may be configured to be capable of selectively outputting two types of electrical stimulation signals, the electrical stimulation signal output from the stimulation generation device 12 for the purpose of evaluating the state of activity of the muscle 50 and the electrical stimulation signal output for the purpose of training the muscle 50, and output one of the electrical stimulation signals between the pair of stimulating electrodes 2a and 2b according to the purpose.

The four myoelectric detection electrodes 3a, 3b, 3c, and 3d are printed and formed at four different positions along the longitudinal direction from the one end, in which the pair of stimulating electrodes 2a and 2b on the bottom surface of the insulating sheet body 4 is integrally formed, toward the other end. When the electrical stimulation position deviates from the body surface of the muscle 50 to be measured, the muscle 50 cannot be stimulated. Moreover, when the myoelectric detection electrodes 3a, 3b, 3c, and 3d deviate from the body surface of the muscle 50 to be measured, muscle action potentials evoked by the electrical stimulation signal cannot be detected. Hence, the myoelectric detection electrode 3d, which is the farthest from the pair of stimulating electrodes 2a and 2b, of the four myoelectric detection electrodes 3a, 3b, 3c, and 3d is printed and formed at a position where the interval between the myoelectric detection electrode 3d and the pair of stimulating electrodes 2a and 2b is shorter than at least the length of the muscle fiber of the muscle 50 of which state of activity is evaluated in order to bring the pair of stimulating electrodes 2a and 2b and all the myoelectric detection electrodes 3a, 3b, 3c, and 3d into intimate contact with the body surface where the muscle 50 exists.

Assume, for example, that the length of the muscle fiber of the vastus lateralis is 65.7 mm and the length of the gastrocnemius muscle is 35.2 mm to 50.7 mm. In the muscle condition measurement sheet 1 used for the evaluation of the state of activity of the vastus lateralis, the interval between the anode 2a and the myoelectric detection electrode 3d, which appear on the bottom surface, is set to equal to or less than 65.7 mm, and in the muscle condition measurement sheet 1 used for the evaluation of the state of activity of the gastrocnemius muscle, the interval between the anode 2a and the myoelectric detection electrode 3d, which appear on the bottom surface, is set to equal to or less than 35.2 mm. Consequently, when the long and slim band-shaped muscle condition measurement sheet 1 is positioned on the body surface along the muscle 50 to be measured, the pair of stimulating electrodes 2a and 2b and all the myoelectric detection electrodes 3a, 3b, 3c, and 3d can come naturally into intimate contact with the body surface without deviating from the position of the muscle 50, securely apply electrical stimulation to the muscle 50, and detect muscle action potentials evoked by the electrical stimulation.

When an electrical stimulation signal innervates the peripheral nerve of the muscle 50 with the pair of stimulating electrodes 2a and 2b, excitation reaches the muscle 50 via the motor nerve to generate, in the muscle 50, muscle action potentials that cause the muscle 50 to contract. The waveform of the muscle action potentials is called the M-wave, which propagates through the muscle 50 from the electrical stimulation position. The M-wave detected by the myoelectric detection electrode 3 in intimate contact with the body surface of the muscle 50 is a waveform of a collective wave of electrical activity of multiple muscle fibers of the muscle 50 to be evaluated. In the embodiment, the propagation speed of the M-wave is obtained based on the difference in time (latency) between when an electrical stimulation signal is applied for the four myoelectric detection electrodes 3a, 3b, 3c, and 3d in intimate contact at the different positions on the body surface and when the rise of the M-wave is detected. The level of fatigue of the muscle 50 is then evaluated.

The reason why an electrical stimulation signal is applied to detect the propagation speed of the M-wave is that the propagation speed of the M-wave of the muscle action potentials evoked by electrical stimulation reflects only a peripheral change such as fatigue of the muscle 50. In other words, a reduction in the propagation speed of the M-wave resulting from muscle fatigue due to exercise is contributed by the central fatigue of the center such as the brain and the motor nerve and the peripheral fatigue of the peripheral muscle cells. However, the propagation speed of the muscle action potential evoked by a weak electrical stimulation signal is reflected only by a change due to the peripheral fatigue. Accordingly, the propagation speed of the M-wave propagating through a muscle cell is compared with one before exercise to enable the objective evaluation of the level of fatigue of the muscle. The propagation speed of the M-wave can be calculated by dividing the distance between the electrical stimulation position and any myoelectric detection electrode 3 by the latency detected from the myoelectric detection electrode 3, or by dividing the distance between a pair of adjacent myoelectric detection electrodes 3 and 3 by the difference between the latencies detected by the pair of myoelectric detection electrodes 3 and 3. However, in the embodiment, the propagation speed of the M-wave is detected by the latter method. The electrical stimulation position may be any position as long as it is a position between the anode 2a and the cathode 2b of the pair of stimulating electrodes. However, as described above, if electrical stimulation lasts for a short period of time, the vicinity of the cathode 2b of the pair of stimulating electrodes 2a and 2b is considered to be the electrical stimulation position for the muscle 50. Therefore, the electrical stimulation position is preferably the position of the cathode 2b.

In any method, the pair of stimulating electrodes 2a and 2b and the myoelectric detection electrodes 3a, 3b, 3c, and 3d, which are formed at the different positions along the muscle fiber direction of the muscle 50, are formed integrally with the insulating sheet body 4. The distance between the electrical stimulation position and the myoelectric detection electrode 3 and the distance between any adjacent pair of the myoelectric detection electrodes 3a, 3b, 3c, and 3d are fixed. Accordingly, the propagation speed of the M-wave can be detected correctly and securely based on the latency of each myoelectric detection electrode 3.

The propagation speed of the M-wave propagating along the muscle 50 is substantially proportional to the width of a nerve fiber in a state where the muscle 50 is not fatigued. If the width is, for example, 0.6 μm, the propagation speed is a six times of 3.6 m/s, and is generally within a range of 3 m/s to 5 m/s. Moreover, the frequency of the M-wave is 100 to 350 Hz. Accordingly, its wavelength is equal to or greater than at least 8.571 mm. However, the center frequency of a normal muscle action potential is equal to or less than 200 Hz. The wavelength is equal to or greater than 15 mm. Accordingly, when the interval between any pair of adjacent myoelectric detection electrodes 3 of the four myoelectric detection electrodes 3a, 3b, 3c, and 3d is set to less than 15 mm, two or more M-waves do not exist between the pair. The propagation speed of the M-wave can be securely detected based on the difference in latency between the adjacent myoelectric detection electrodes 3. Hence, in the embodiment, the four myoelectric detection electrodes 3a, 3b, 3c, and 3d are caused to appear on the bottom surface of the muscle condition measurement sheet 1 spaced at regular intervals of 10 mm.

The myoelectric detection electrodes 3a, 3b, 3c, and 3d are extended to the other end side (the left end side in the drawings) by the lead patterns 6a, 6b, 6c, and 6d wired along the bottom surface of a tale portion 4a of the insulating sheet body 4. The myoelectric detection electrodes 3a, 3b, 3c, and 3d are respectively connected to non-inverting inputs of the four comparison circuits 13a, 13b, 13c, and 13d via connection cables. A muscle action potential detected by each of the myoelectric detection electrodes 3a, 3b, 3c, and 3d has a voltage as weak as several mV. Accordingly, a flat surface of the tale portion 4a is covered with a grounded shield conductor (not illustrated) to prevent the entry of noise. Moreover, the myoelectric detection electrodes 3a, 3b, 3c, and 3d are formed at the different positions of the insulating sheet body 4. Accordingly, the lengths of the lead patterns 6a, 6b, 6c, and 6d extended to the other end side are also different. However, the pattern width is increased in proportion to the length to make the resistance values of all the lead patterns 6a, 6b, 6c, and 6d the same. Consequently, the muscle action potentials detected by the myoelectric detection electrodes 3a, 3b, 3c, and 3d do not include errors due to differences in the resistance values of the lead patterns 6a, 6b, 6c, and 6d.

The lead patterns 6a, 6b, 6c, and 6d are wired on the bottom surface, which faces the body surface, of the insulating sheet body 4. Accordingly, their surfaces are covered with a resist to be insulated from the body surface.

Moreover, as illustrated in FIG. 3, the grounded ground electrode 5 to block noise passing along the insulating sheet body 4 is printed and formed on the flat surface of the insulating sheet body 4 between the pair of stimulating electrodes 2a and 2b and the myoelectric detection electrodes 3a, 3b, 3c, and 3d.

A description is given of a method for evaluating the level of fatigue of the biceps brachii 50 in the evaluation system 10 using the muscle condition measurement sheet 1. Firstly, the release paper of the double-sided tape adhered to the bottom surface of the muscle condition measurement sheet 1 is peeled off. As illustrated in FIG. 1, the muscle condition measurement sheet 1 is adhered to the body surface of the muscle 50 and positioned in such a manner as that the muscle fiber direction of the muscle 50 to be evaluated agrees with the longitudinal direction of the long and slim band-shaped muscle condition measurement sheet 1. Consequently, the pair of stimulating electrodes 2a and 2b and the myoelectric detection electrodes 3a, 3b, 3c, and 3d naturally come into intimate contact with the body surface of the muscle 50 along the direction of the muscle fiber.

Next, before the onset of an exercise to contract and expand the muscle 50, an electrical stimulation signal of a square wave with a pulse width of 0.5 msec and a voltage of 100 V is output at intervals of one second between the pair of stimulating electrodes 2a and 2b from the stimulation generation device 12 via the isolator 11. The potentials of the myoelectric detection electrodes 3a, 3b, 3c, and 3d with respect to the ground potential of the reference electrode 2b are continuously output from the comparison circuits 13a, 13b, 13c, and 13d during the passage of a fixed time after the output of the electrical stimulation signal. The output waveform of the comparison circuits 13a, 13b, 13c, and 13d is the M-wave being the waveform of the muscle action potentials evoked by the electrical stimulation signal and detected by the myoelectric detection electrodes 3a, 3b, 3c, and 3d. The comparison circuits 14a, 14b, and 14c connected downstream of the comparison circuits 13a, 13b, 13c, and 13d output, to the logger 15, the differences between the potentials of the M-wave detected by the adjacent pairs of the myoelectric detection electrodes 3a, 3b, 3c, and 3d.

The reason why the comparison circuits 14a, 14b, and 14c take the differences between the potentials of the M-wave detected by any adjacent pair of the myoelectric detection electrodes 3a, 3b, 3c, and 3d is to cancel the influence of superimposed common-mode noise common to the M-waves detected by the myoelectric detection electrodes 3a, 3b, 3c, and 3d.

Figure 5:
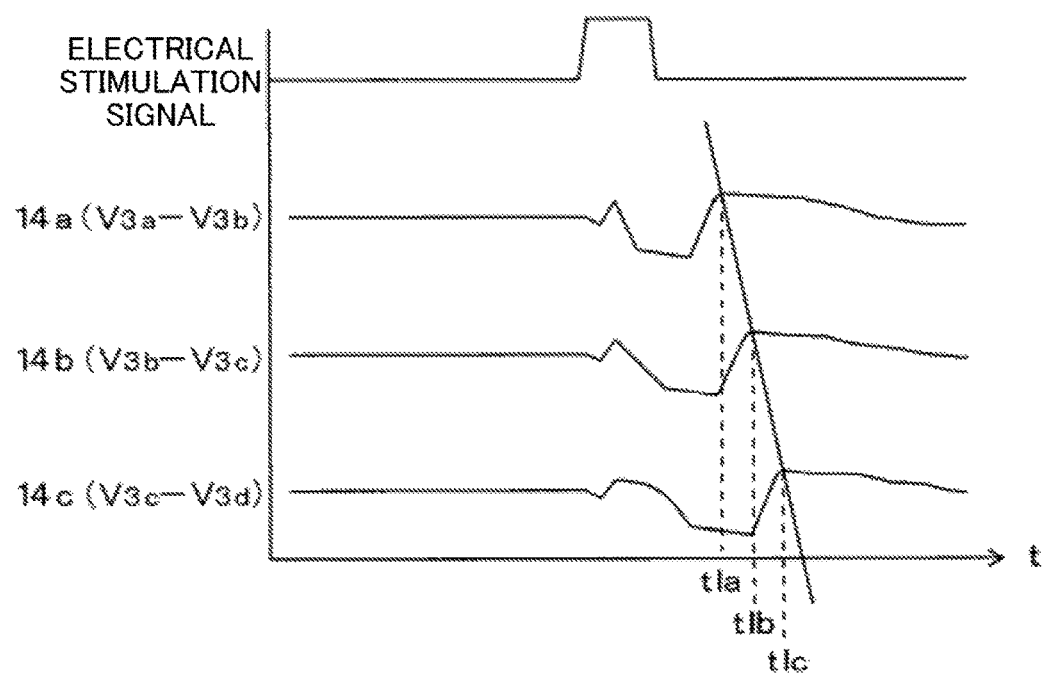
FIG. 5 is a waveform diagram illustrating an evoked electromyogram EMG detected by myoelectric detection electrodes 3 in intimate contact at different positions with a body surface at the onset of exercise.

FIG. 5 is an evoked electromyogram EMG representing, with elapsed time, the differences between the potentials of the M-wave detected by the myoelectric detection electrodes 3a, 3b, 3c, and 3d in output waveforms output from the comparison circuits 14a, 14b, and 14c to the logger 15 before the onset of the exercise to contract and expand the muscle 50. In other words, the output waveform of the comparison circuit 14a is a differential voltage waveform between a voltage V3a of the M-wave detected by the myoelectric detection electrode 3a and a potential V3b of the M-wave detected by its adjacent muscle detection electrode 3b (V3a-V3b). The output waveform of the comparison circuit 14b is a differential voltage waveform between the potential V3b of the M-wave detected by the myoelectric detection electrode 3b and a potential V3c of the M-wave detected by its adjacent myoelectric detection electrode 3c (V3b-V3c). The output waveform of the comparison circuit 14c is a differential voltage waveform between the potential V3c of the M-wave detected by the myoelectric detection electrode 3c and a potential V3d of the M-wave detected by its adjacent myoelectric detection electrode 3d (V3c-V3d).

The myoelectric detection electrodes 3a, 3b, 3c, and 3d are in intimate contact with the body surface, at positions spaced at regular intervals along the direction of the muscle fiber of the muscle 50 from the myoelectric detection electrode 3a, the distance of which to the pair of stimulating electrodes 2a and 2b is the shortest, to the myoelectric detection electrode 3d. Accordingly, the M-wave generated by the electrical stimulation signal around the cathode 2b propagates along the muscle fiber of the muscle 50. The rise of the M-wave is detected in the order of the myoelectric detection electrodes 3a, 3b, 3c, and 3d, which is the order of contact positions. For example, at the point of time when the M-wave reaches the position of the myoelectric detection electrode 3a and V3a increases, the potential V3b of the myoelectric detection electrode 3b, which the M-wave has not reached, is constant. Accordingly, the differential voltage waveform (V3a-V3b) being the output of the comparison circuit 14a increases. In other words, time t1a when the rise of the differential voltage waveform (V3a-V3b) was observed can be regarded as the time when the rise of the M-wave was detected by the myoelectric detection electrode 3a. The time elapsed between the output of the electrical stimulation signal and t1a is the latency of the myoelectric detection electrode 3a. Similarly, the time elapsed between the output of the electrical stimulation signal and the time when the rise of the differential voltage waveform (V3b-V3c) was observed, t1b, is the latency of the myoelectric detection electrode 3b. The time elapsed between the output of the electrical stimulation signal and the time when the rise of the differential voltage waveform (V3c-V3d) was observed, t1c, is the latency of the myoelectric detection electrode 3c.

FIG. 5 represents the output waveforms of the comparison circuits 14a, 14b, and 14c at regular intervals on the vertical axis, corresponding to the arrangement of the myoelectric detection electrodes 3a, 3b, and 3c at regular intervals. Accordingly, the gradient of a straight line linking the differential voltage (V3a-V3b) at time t1a, the differential voltage (V3b-V3c) at time t1b, and the differential voltage (V3c-V3d) at time t1c, time t1a, time t1b, and time t1c being the times when the rise was observed, represents the propagation speed of the M-wave. The data processing device 16 calculates the propagation speed of the M-wave based on the differential voltages (V3a-V3b), (V3b-V3c), and (V3c-V3d) recorded in the logger 15 and the intervals between the myoelectric detection electrodes 3a, 3b, and 3c. In the embodiment, the propagation speed of the M-wave before the onset of the exercise to contract and expand the muscle 50 is calculated as 4.77 m/s based on the differential voltage waveforms (V3a-V3b), (V3b-V3c), and (V3c-V3d) represented in FIG. 5 and the actual measured intervals between the myoelectric detection electrodes 3a, 3b, and 3c.

Next, after an exercise to exert the strength of the biceps brachii 50 for five seconds and then rest it for five seconds is repeated 11 times, the same electrical stimulation signal is similarly output to detect the M-wave evoked by the electrical stimulation signal based on the potentials of the myoelectric detection electrodes 3a, 3b, and 3c. The latencies of the myoelectric detection electrodes 3a, 3b, and 3c are obtained based on times t1a', t1b', and t1c' when the rise of the M-wave was detected in the output waveforms of the comparison circuits 14a, 14b, and 14c illustrated in FIG. 6. The propagation speed of the M-wave of the muscle 50, which was fatigued after the exercise, is calculated.

Figure 6:
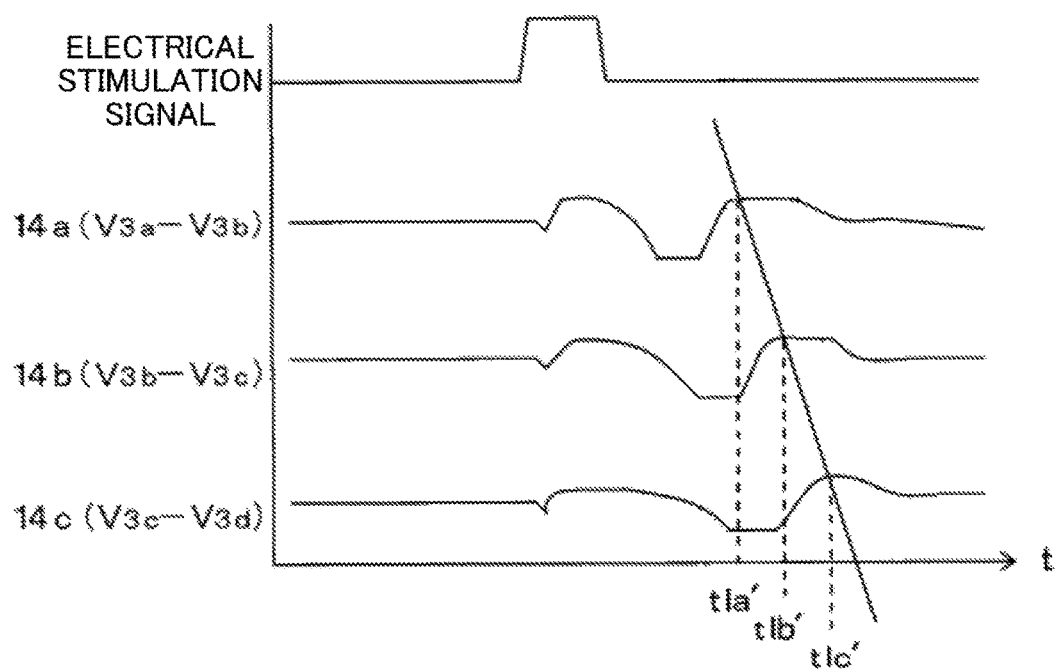
FIG. 6 is a waveform diagram illustrating an evoked electromyogram EMG detected by the myoelectric detection electrodes 3 in intimate contact at the different positions with the body surface immediately after the end of exercise.

In FIG. 6, the gradient, which represents the propagation speed of the M-wave, of the straight line linking the differential voltage (V3a-V3b) at time t1a, the differential voltage (V3b-V3c) at time t1b, and the differential voltage (V3c-V3d) at time t1c is a gentler gradient than that of FIG. 5. The propagation speed of the M-wave in the state where the muscle 50 was fatigued was calculated as 3.77 m/s based on the differential voltages (V3a-V3b), (V3b-V3c), and (V3c-V3d) at time t1a', t1b', and t1c' and the actual measured intervals between the myoelectric detection electrodes 3a, 3b, and 3c. In this manner, when the muscle 50 repeats contraction and expansion during exercise for a fixed period of time, lactic acid is produced in a part of the muscle 50 due to the lack of supply of oxygen, which leads to the state of muscle fatigue in which the contractile force of the muscle 50 is reduced. Accordingly, the propagation speed of the M-wave is also reduced.

Therefore, the level of fatigue of the muscle 50 can be numerically evaluated by use of the muscle condition measurement sheet 1 according to the embodiment based on the propagation speed of the M-wave calculated in real time during exercise in which a load is applied to the muscle 50.

A muscle condition measurement sheet 20 according to a second embodiment of the present invention is formed integrally with a plurality of myoelectric detection electrodes 21 (m, n) distributed to different positions on a bottom surface of an insulating sheet body 22. The muscle condition measurement sheet 20 and an evaluation system 18 using the muscle condition measurement sheet 20 are described below with reference to FIGS. 7 to 11B. Units of the muscle condition measurement sheet 20 and the evaluation system 18, the units being configured to act in the same manner as or similarly to those of the above-mentioned muscle condition measurement sheet 1 and evaluation system 10, use the same numerals, and their detailed descriptions are omitted.

Figure 9:
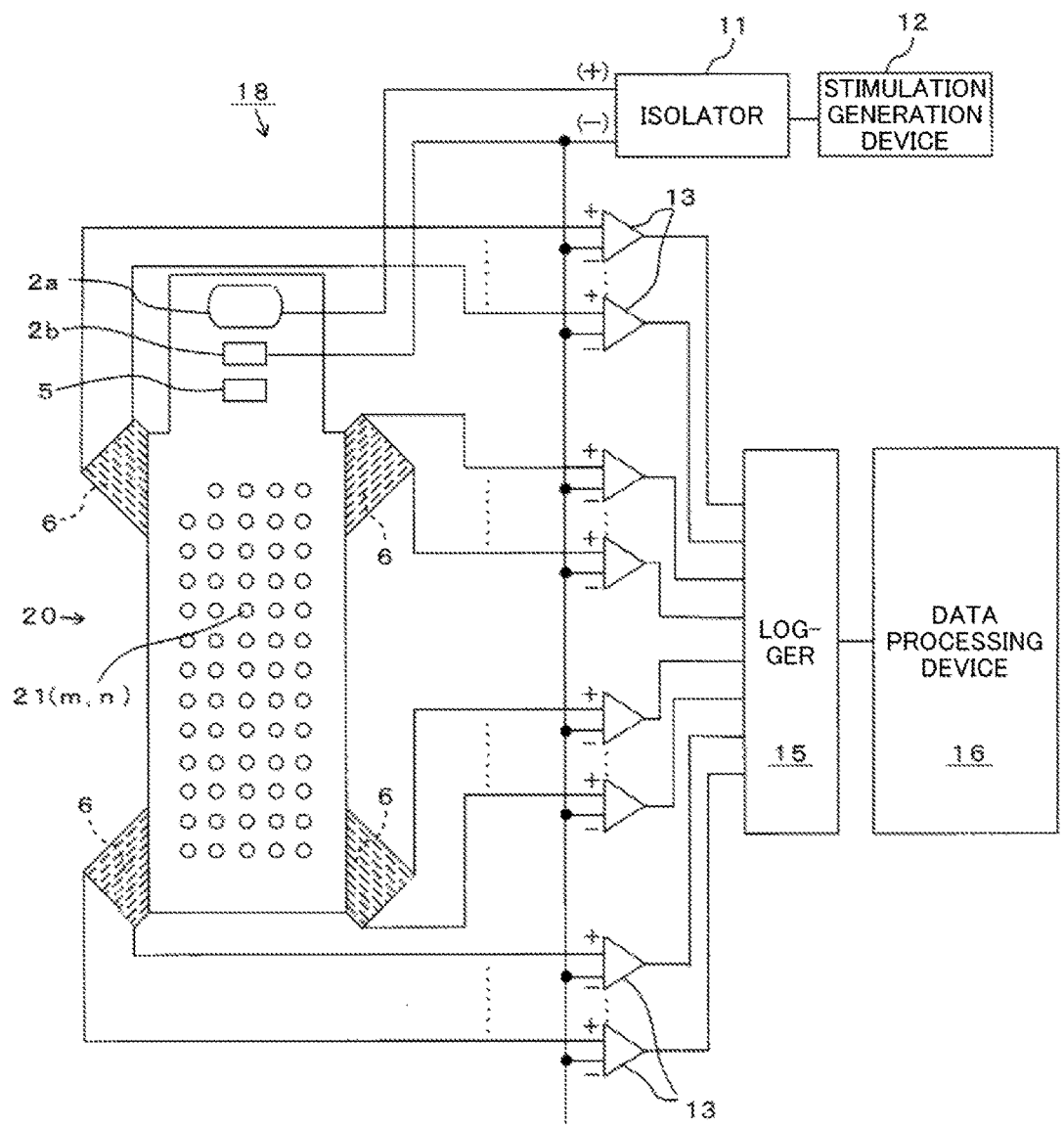
FIG. 9 is a block diagram of an evaluation system 18 that uses the muscle condition measurement sheet 20 according to the second embodiment of the invention of the present application.

The evaluation system 18 using the muscle condition measurement sheet 20 evaluates the state of activity of the trapezius 50 of which muscle fibers travel in different directions. As illustrated in FIG. 9, the evaluation system 18 includes the stimulation generation device 12 that outputs an electrical stimulation signal via the isolator 11 between the pair of stimulating electrodes 2, the anode 2a and the cathode 2b, of the muscle condition measurement sheet 20, 64 comparison circuits 13, 13 . . . that respectively compare the potentials of 64 myoelectric detection electrodes 21 (m, n) of the muscle condition measurement sheet 20 with the ground potential of the reference electrode 2b, and respectively output muscle action potentials detected by the myoelectric detection electrodes 21 (m, n) to the logger 15, the logger 15 that records the muscle action potentials output from the comparison circuits 13, 13 . . . together with elapsed time, and the data processing device 16 that evaluates the level of fatigue of the muscle 50 and the propagation direction of the muscle action potential based on the results recorded in the logger 15.

Figure 7:
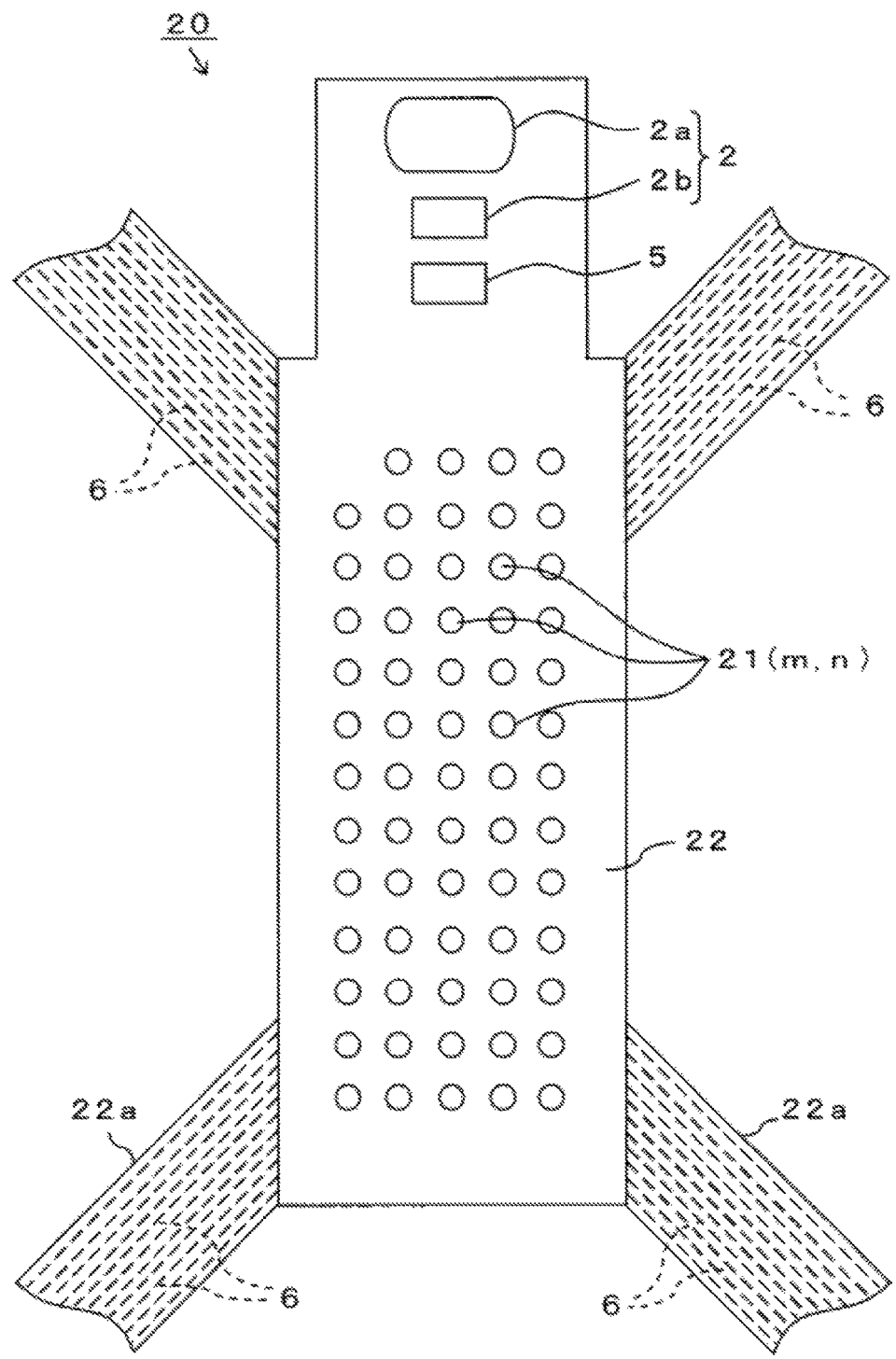
FIG. 7 is a bottom view of a muscle condition measurement sheet 20 according to a second embodiment.
Figure 8:
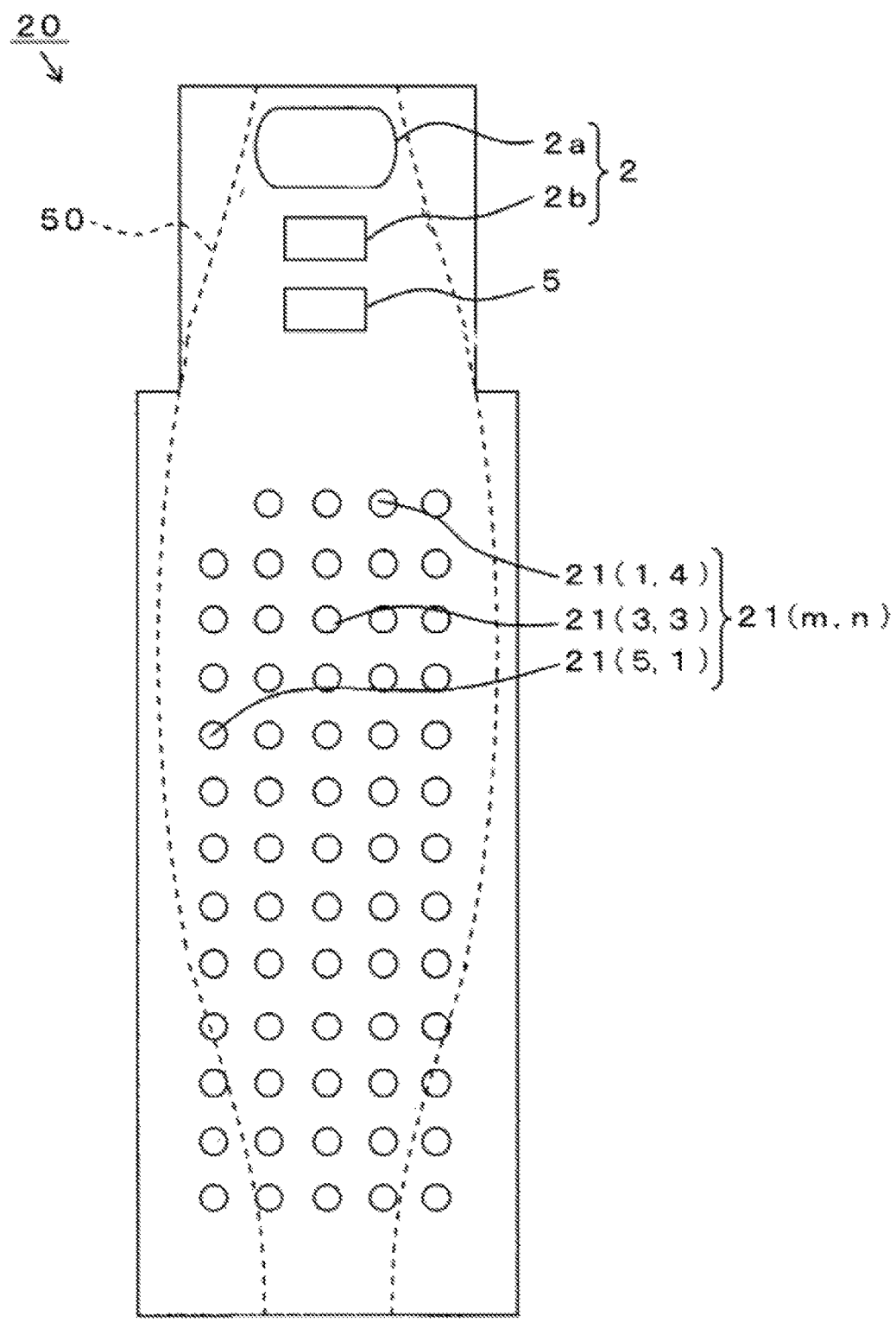
FIG. 8 is a main part plan view of the muscle condition measurement sheet 20 in intimate contact with a body surface of a muscle 50 to be measured.

As illustrated in FIGS. 7 and 8, the muscle condition measurement sheet 20 is formed of a flexible print circuit on which the pair of stimulating electrodes 2 including the anode 2a and the cathode 2b, the ground electrode 5, the 64 myoelectric detection electrodes 21 (m, n), and 64 lead patterns 6 connected respectively to the myoelectric detection electrodes 21 (m, n) are printed and formed on the bottom side of the flexible insulating sheet body 22 made of PET or the like. The 64 myoelectric detection electrodes 21 (m, n) appear at positions of a matrix with 15 rows and 5 columns along left and right parallel outlines of the bottom surface, except a position at the first row and the first column on the left upper corner of the bottom surface of the insulating sheet body 22. The 64 lead patterns 6 are respectively wired from the myoelectric detection electrodes 21 (m, n) to tale portions 22a at the four corners of the insulating sheet body 22. The 64 lead patterns 6 are respectively connected to non-inverting inputs of the 64 comparison circuits 13, 13 . . . via connection cables. A surface, which faces a body surface, of the lead pattern 6 is also covered with a resist to be insulated from the body surface.

As illustrated, the anode 2a of the pair of stimulating electrodes 2 has an oval-shaped outline, and the cathode 2b has a rectangular outline. The anode 2a and the cathode 2b are exposed from the bottom surface of the insulating sheet body 22. However, both of their exposure areas that are exposed from the back surface are equal to or greater than 100 mm$^2$. Accordingly, even if an electrical stimulation signal with a current value of 5 mA or more is applied, electrical stimulation does not cause pain.

Moreover, in the embodiment, the ground electrode 5 appears between the cathode 2b and the myoelectric detection electrodes 21 (m, n), which are on the bottom side of the insulating sheet body 22. Consequently, noise flowing along the body surface between the stimulating electrode 2 and the myoelectric detection electrodes 21 (m, n) is blocked.

The insulating sheet body 22 is formed into a shape that covers a body surface of a major part of the trapezius 50. Release paper of unillustrated double-sided tape attached to the entire bottom surface excluding sites where the pair of stimulating electrodes 2a and 2b, the ground electrode 5, and the 64 myoelectric detection electrodes 21 (m, n) are exposed is peeled off, and then an adhesive layer appears. The adhesive layer is adhered to the body surface of the trapezius 50 to position the muscle condition measurement sheet 20 on the body surface of the trapezius 50.

The muscle condition measurement sheet 20 is positioned on the body surface of the trapezius 50. Accordingly, the pair of stimulating electrodes, the anode 2a and the cathode 2b, come into intimate contact with the body surface on one side of the trapezius 50, and also the 64 myoelectric detection electrodes 21 (m, n) come into intimate contact at the different positions distributed on the body surface of the trapezius 50, and one, two or more myoelectric detection electrodes 21 (m, n) come into intimate contact with a body surface of the multiple muscle fibers, which travel in different directions, of the trapezius 50.

The muscle condition measurement sheet 20 according to the embodiment causes the multiple myoelectric detection electrodes 21 (m, n) to appear on the bottom surface of the flexible insulating sheet body 22, distributed to different positions on a flat surface. Accordingly, even if the state of activity of the trapezius 50 in which the muscle fibers travel in the different directions is evaluated, the insulating sheet body 22 bends along the curved body surface so that the multiple myoelectric detection electrodes 21 (m, n) can be brought into intimate contact along the curved body surface of the entire trapezius 50.

The myoelectric detection electrodes 21 (13, n) that are the farthest from the pair of stimulating electrodes 2a and 2b are printed and formed at positions where the interval between the myoelectric detection electrodes 21 (13, n) and the pair of stimulating electrodes 2a and 2b is shorter than the length of the muscle fiber of the trapezius 50 to bring the pair of stimulating electrodes 2a and 2b and all the myoelectric detection electrodes 21 (m, n) into intimate contact with the body surface of the trapezius 50. Consequently, it is possible to bring all the myoelectric detection electrodes 21 (m, n) into intimate contact with the body surface without deviating from the position of the trapezius 50, securely apply electrical stimulation to the trapezius 50, and detect muscle action potentials evoked by electrical stimulation.

A general muscle 50 is thick in the middle in the muscle fiber direction along the direction of the muscle fibers, and its body surface has a complicated curved surface. Accordingly, the myoelectric detection electrodes 21 (m, n) may also be formed in such a manner as to protrude from the bottom surface of the insulating sheet body 22, as in the pair of stimulating electrodes 2a and 2b, to bring more myoelectric detection electrodes 21 (m, n) into intimate contact along the curved body surface of the muscle 50.

Figure 10:
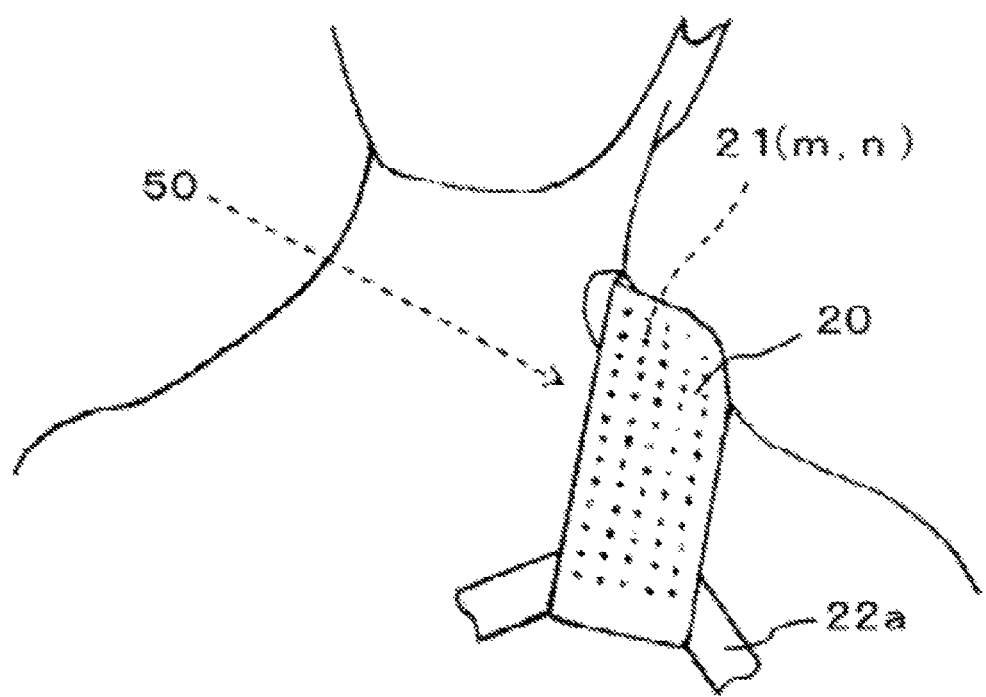
FIG. 10 is an external view illustrating the state where the muscle condition measurement sheet 20 is in intimate contact with the body surface of the trapezius 50 of which state of activity is evaluated.

In the evaluation system 18 using the muscle condition measurement sheet 20, the muscle condition measurement sheet 20 is positioned in intimate contact with the body surface of the trapezius 50 as illustrated in FIG. 10. An electrical stimulation signal is output from the stimulation generation device 12 to the pair of stimulating electrodes 2a and 2b to enable the evaluation of a change in the active region and level of fatigue of the trapezius 50 in accordance with muscle fatigue and a change in voluntary muscle strength.

When a change in the active region in accordance with the level of fatigue of the trapezius 50 is evaluated, muscle action potentials of all the myoelectric detection electrodes 21 (m, n) output from the comparison circuits 13, 13 . . . are recorded in the logger 15 at intervals of fixed elapsed time while the trapezius 50 is continuously being contracted and expanded. The data processing device 16 generates an evoked electromyogram EMG representing the muscle action potentials at the positions of the myoelectric detection electrodes 21 (m, n) recorded in the logger 15. The level of the muscle action potentials represents the number of motor units recruited and their firing rates at the contact position of the myoelectric detection electrode 21 (m, n) that has detected the muscle action potentials. Accordingly, the generated evoked electromyogram EMG represents a site where the muscle fibers are activated and a site where not activated among the muscle fibers, which travel in multiple directions, of the trapezius 50. When evoked electromyograms EMG generated at intervals of the fixed elapsed time are compared, a situation can be seen in which the recruitment/derecruitment of motor units changes at each position of the trapezius 50 and the motor units of the trapezius 50 are alternatingly activated until total fatigue.

Moreover, when a change in the active region of the trapezius 50 for the change in the voluntary muscle strength of the trapezius 50 is evaluated, for example, the motor task of the trapezius 50 is changed in stages from a resting state to a maximal voluntary contraction (MVC: maximal voluntary contraction). Muscle action potentials of all the myoelectric detection electrodes 21 (m, n) output from the comparison circuits 13, 13 . . . are similarly recorded in the logger 15 at each voluntary muscle strength. In the data processing device 16, an evoked electromyogram EMG is generated based on the muscle action potentials at the position of each myoelectric detection electrode 21 (m, n) recorded in the logger 15. Consequently, it is possible to evaluate which region in the trapezius 50 the motor units are activated according to the change of the voluntary muscle strength.

When the level of fatigue of the trapezius 50 is evaluated, the propagation speed, along the muscle 50, of the M-wave evoked in the trapezius 50 by an electrical stimulation signal output from the stimulation generation device 12 is detected before and after exercise as in the first embodiment. The level of fatigue of the trapezius 50 is evaluated based on the propagation speed of the M-wave. In the muscle condition measurement sheet 20, unlike the muscle condition measurement sheet 1 in which the four myoelectric detection electrodes 3a, 3b, 3c, and 3d are arranged in a straight line, the 64 myoelectric detection electrodes 21 (m, n) are placed, distributed to positions in the multiple directions from the electrical stimulation position of the pair of stimulating electrodes 2a and 2b. Accordingly, the propagation speed of the M-wave that propagates along the muscle fibers travelling in the different directions can be detected based on the latencies of the myoelectric detection electrodes 21 (m, n) in the detection of the M-wave and the interval between the stimulating electrodes 2a and 2b.

Figure 11A:
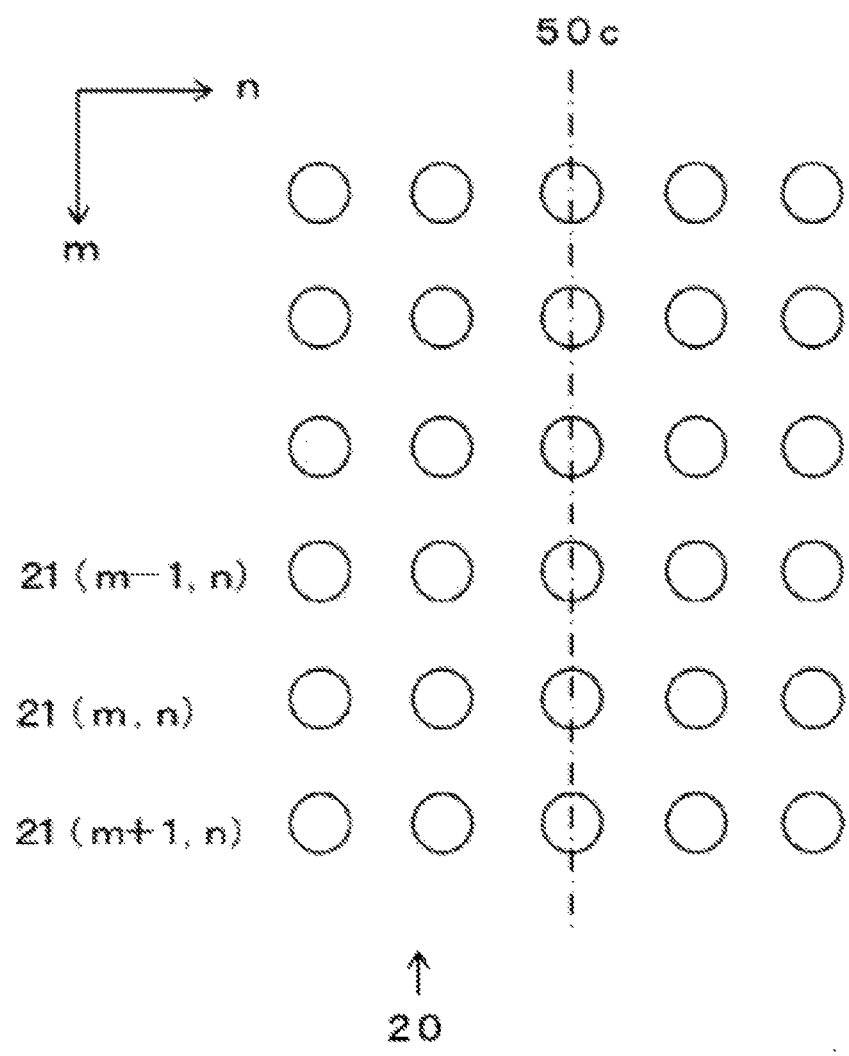
FIG. 11A illustrates the relationship between a muscle fiber direction 50C of the muscle 50 to be measured and the muscle condition measurement sheet 20, and is an explanatory view illustrating a state where the muscle condition measurement sheet 20 is positioned along the muscle fiber direction 50C of the muscle 50.

Moreover, when the propagation speed of the M-wave of the muscle 50 in which the muscle fiber direction 50C is clear, such as the soleus and the biceps brachii, is detected, as illustrated in FIG. 11A, the muscle condition measurement sheet 20 is positioned on the body surface such that the column direction of the myoelectric detection electrodes 21 (m, n) arranged with m rows and n columns agrees with the muscle fiber direction 50C. The propagation speed of the M-wave that propagates along the muscle fiber direction 50C of the muscle 50 is detected based on the latencies detected by the myoelectric detection electrodes 21 (m, n) at each row and the intervals between the rows.

Figure 11B:
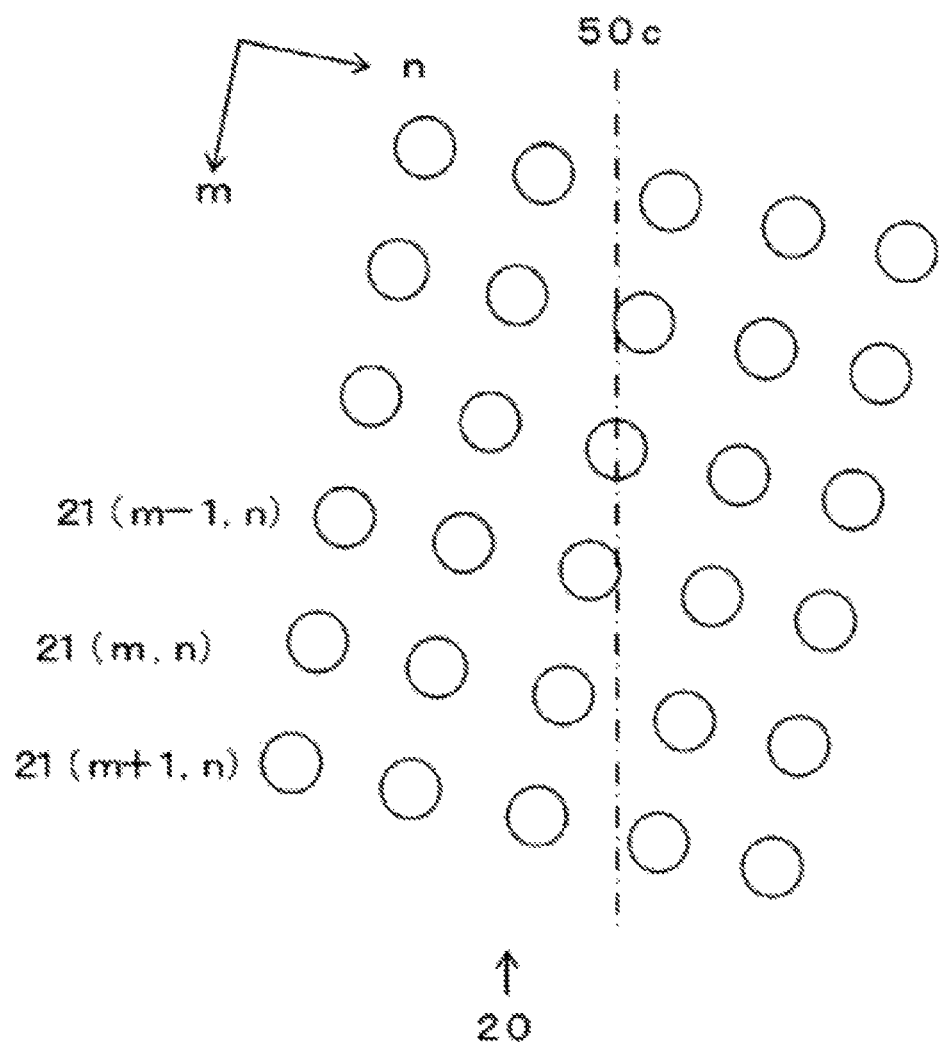
FIG. 11B illustrates the relationship between a muscle fiber direction 50C of the muscle 50 to be measured and the muscle condition measurement sheet 20, and is an explanatory view illustrating a state where the muscle condition measurement sheet 20 is positioned inclined with respect to the muscle fiber direction 50C of the muscle 50.

However, there is a case where the muscle fiber direction 50C of the muscle 50 is not clear and the column direction of the myoelectric detection electrodes 21 (m, n) does not agree with the muscle fiber direction 50C as illustrated in FIG. 11B. In the muscle condition measurement sheet 20 according to the embodiment, even in such a case, since any myoelectric detection electrode 21 (m, n) at each row is placed in close proximity to the muscle 50 along the muscle fiber direction 50C, the propagation speed of the M-wave can be detected with a given accuracy based on the latency of the myoelectric detection electrode 21 (m, n) placed in close proximity and the interval between the myoelectric detection electrodes 21 (m, n) placed in close proximity at each row. In terms of the myoelectric detection electrodes 21 (m, n) placed in closest proximity to the muscle fiber direction 50C, the latencies and amplitude levels of the M-wave detected by the myoelectric detection electrodes 21 (m, n) at each row can be compared and extracted. If the extraction of the myoelectric detection electrodes 21 (m, n) in close proximity to the muscle fiber direction 50C of the muscle 50 is complicated, an average or total sum of the latencies of the myoelectric detection electrodes 21 (m, n) may be calculated on a row by row basis to detect the propagation speed of the M-wave based on the calculated value and the interval between the rows.

A muscle condition measurement sheet 40 according to a third embodiment of the present invention is a modification of the above-mentioned muscle condition measurement sheet 20 used in the evaluation system 18. A plurality of myoelectric detection electrodes 41 (r, q) is exposed distributed on a plurality of circles arranged concentrically centered on one of a pair of stimulating electrodes 43a and 43b, an anode 43a, being exposed from a bottom surface of an insulating sheet body 42. The muscle condition measurement sheet 40 is described below, with reference to FIG. 12. However, configurations that act in the same manner as or similarly to the muscle condition measurement sheet 20 and the evaluation system 18 according to the second embodiment use the same numerals in FIG. 12, and their detailed descriptions are omitted.

Figure 12:
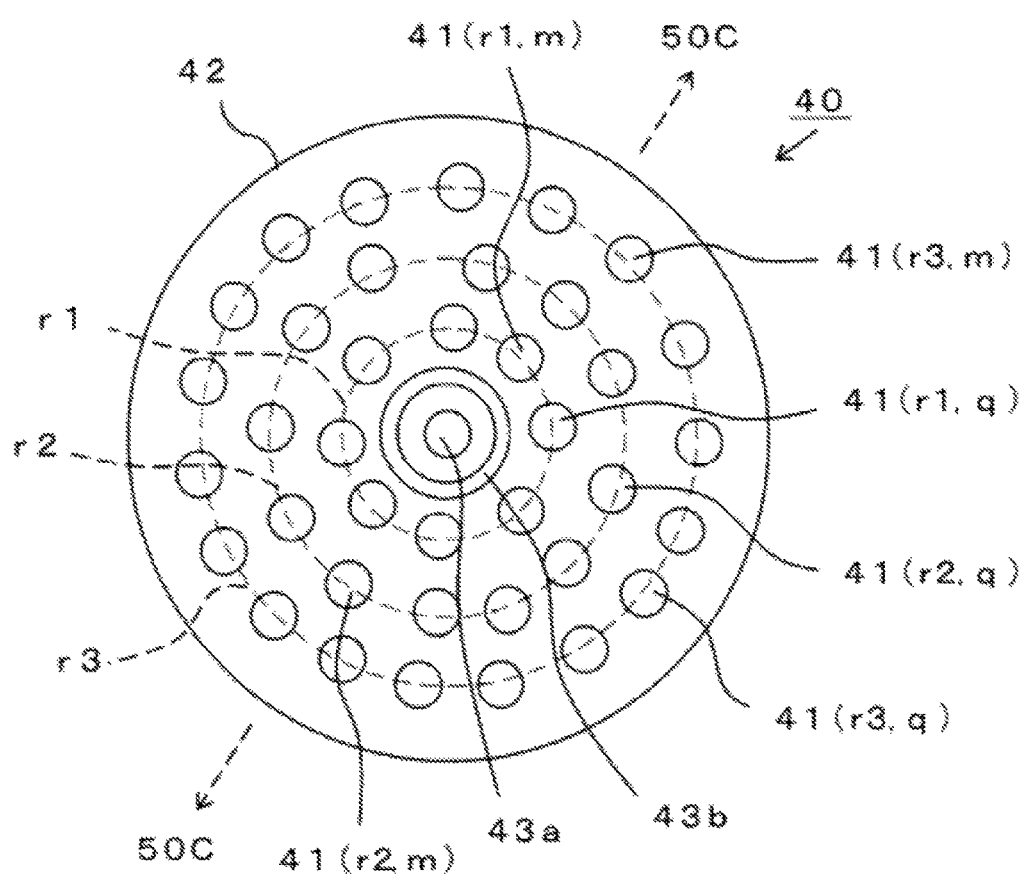
FIG. 12 is a bottom view of a muscle condition measurement sheet 40 according to a third embodiment.

In terms of the muscle condition measurement sheet 40, the pair of stimulating electrodes 43a and 43b and the plurality of myoelectric detection electrodes 41 (r, q) are distributed, exposed from the bottom side of the flexible circular insulating sheet body 42, and insulated from each other as illustrated in FIG. 12. The anode 43a of the pair of stimulating electrodes 43a and 43b is exposed in a circular form at the center of the circular insulating sheet body 42. The cathode 43b being the other stimulating electrode is exposed in a ring form around the anode 43a. The anode 43a and the cathode 43b are respectively connected to the isolator 11 via unillustrated electric wires.

In terms of the plurality of myoelectric detection electrodes 41 (r, q), q myoelectric detection electrodes 41 (r, q) are exposed spaced at regular angular intervals along circumferential directions of three kinds of virtual concentric circles r1, r2, and r3 that center the exposed position of the anode 43a. The q myoelectric detection electrodes 41 (r, q) are respectively connected to the non-inverting inputs of the comparison circuits 13, 13 . . . via the lead patterns 6 wired to the unillustrated tale portions 22a. In the embodiment, the intervals between the virtual concentric circles r1, r2, and r3 are even. However, the number of the virtual concentric circles r and their radii can be freely set. Moreover, the plurality of myoelectric detection electrodes 41 (r, q) may be exposed at positions on radial lines where a straight line passing through the center of the exposed position of the anode 43a intersects the virtual concentric circles r1, r2, and r3.

The muscle condition measurement sheet 40 is placed such that the center of the circular insulating sheet body 42 is on the body surface of the muscle 50 to be evaluated. Release paper of unillustrated double-sided tape is peeled off, and then an adhesive layer appears. The adhesive layer is adhered to the body surface to position the muscle condition measurement sheet 40 on the body surface of the muscle 50. Consequently, the pair of stimulating electrodes 43a and 43b comes into intimate contact with the body surface of the muscle 50 to be evaluated to bring the plurality of myoelectric detection electrodes 41 (r, q) into intimate contact respectively at the positions distributed in directions toward the periphery of the body surface centering the anode 43a. Therefore, one or two or more myoelectric detection electrodes 41 (r, q) along the direction of the muscle fibers of the muscle 50 from the contact position of the anode 43a come into intimate contact with the body surface of the muscle 50.

When the state of activity of the muscle 50 is evaluated in the evaluation system 18 using the muscle condition measurement sheet 40, the stimulation generation device 12 outputs an electrical stimulation signal to the pair of stimulating electrodes 43a and 43b first. The levels of the evoked myoelectric signal output from all the myoelectric detection electrodes 41 (r, q) via the comparison circuits 13, 13 . . . are compared. The evoked myoelectric signal evoked by the electrical stimulation signal propagates along the longitudinal direction of the muscle fiber; accordingly, it is possible to presume that among the myoelectric detection electrodes 41 (r, q) exposed on the same virtual concentric circle r, myoelectric detection electrodes having a relatively high level of the evoked myoelectric signal (hereinafter referred to as the specific myoelectric detection electrode 41 (r, m)) is in intimate contact with a body surface near the muscle 50. Therefore, in the muscle condition measurement sheet 40 according to the embodiment, even if the muscle fiber direction 50C of the muscle 50 is not clear, the pair of stimulating electrodes 43a and 43b and the specific myoelectric detection electrode 41 (r, m) are placed along the muscle fiber direction 50C and accordingly the propagation speed of the M-wave can be detected with a given accuracy based on the latency of the specific myoelectric detection electrode 41 (r, m) and the radius of the virtual concentric circle r on which the specific myoelectric detection electrode 41 (r, m), that is, the interval between the anode 43a at the electrical stimulation position and the specific myoelectric detection electrode 41 (r, m).

Moreover, in the evaluation system 18 using the muscle condition measurement sheet 40, the plurality of myoelectric detection electrodes 41 (r, q) is exposed at the positions distributed in the multiple directions from the center where the pair of stimulating electrodes 43a and 43b is exposed. Accordingly, evoked myoelectric signals detected by the plurality of myoelectric detection electrodes 41 (r, q) are compared; accordingly, the presence or absence of the surrounding muscle 50 centering the electrical stimulation position and the composition of the muscle 50 can be obtained.

Figure 13:
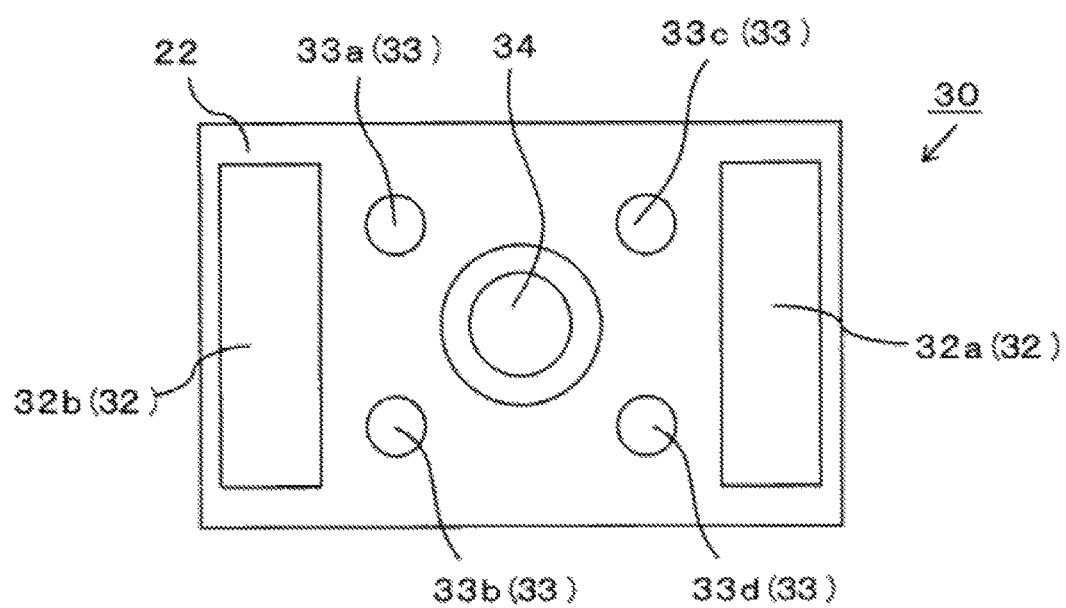
FIG. 13 is a bottom view of a muscle condition measurement sheet 30 according to a fourth embodiment.
Figure 14:
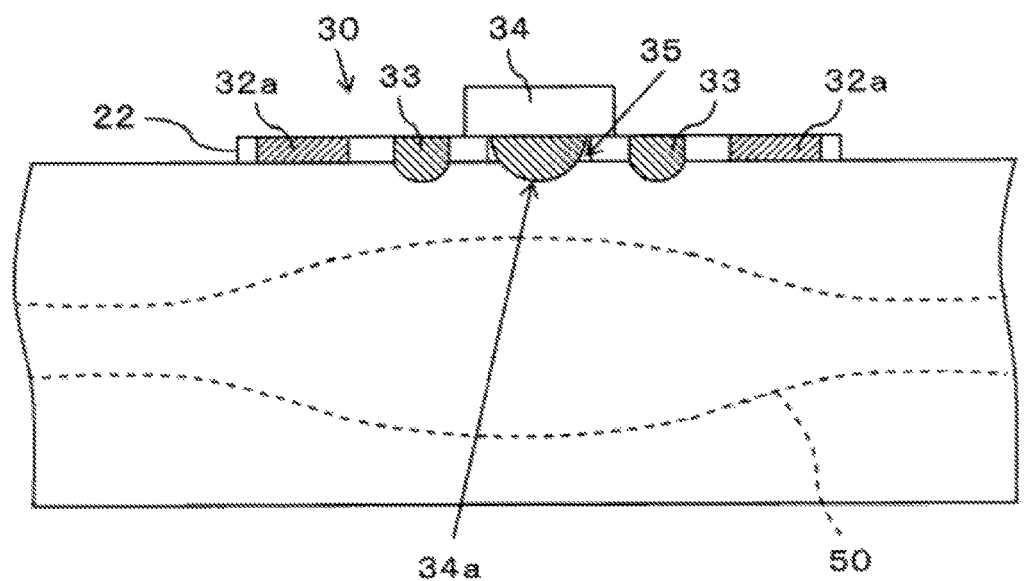
FIG. 14 is a cross-sectional view illustrating a state where the muscle condition measurement sheet 30 is in intimate contact with a body surface of a muscle 50 to be measured.
Figure 15:
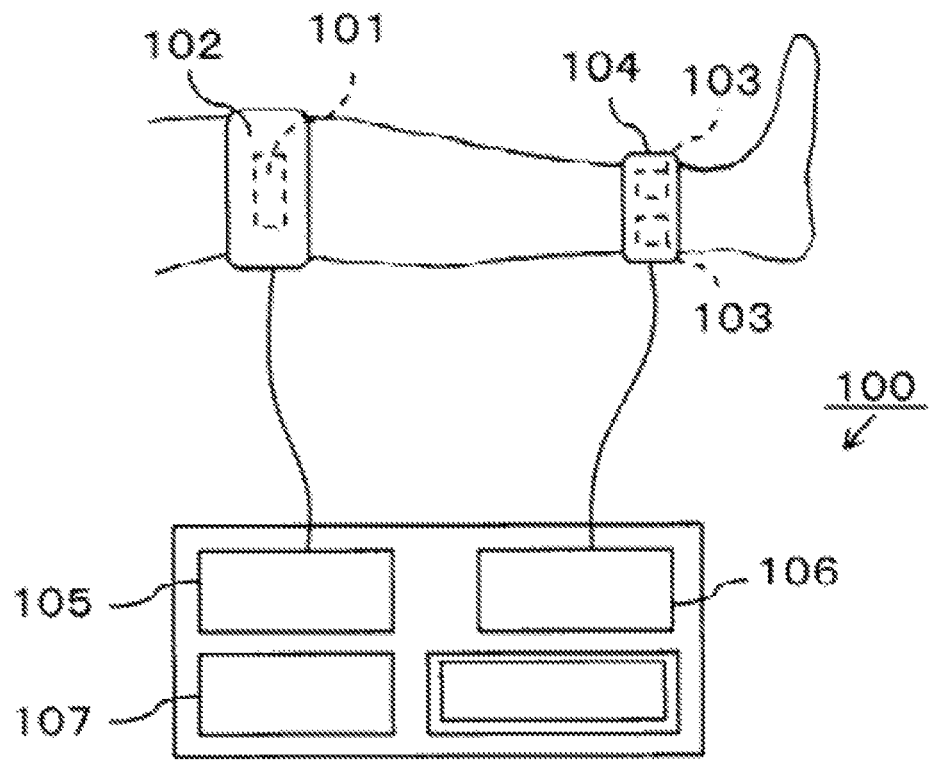
FIG. 15 is a configuration diagram of a related evoked electromyography apparatus 100.

FIGS. 13 and 14 illustrate a muscle condition measurement sheet 30 according to a fourth embodiment of the present invention. An evaluation system using the muscle condition measurement sheet 30 evaluates the propagation speed of the M-wave evoked by electrical stimulation and the level of fatigue of the muscle 50 based on muscle sound produced by mechanical displacement of the muscle 50 that contracts and expands by electrical stimulation. The muscle condition measurement sheet 30 is formed by integrating a mechanomyography sensor 34, in addition to a pair of stimulating electrodes 32 including an anode 32a and a cathode 32b, and four myoelectric detection electrodes 33a, 33b, 33c, and 33d, into the insulating sheet body 22. The muscle condition measurement sheet 30 and the evaluation system using the muscle condition measurement sheet 30 are described below. However, the evaluation system using the muscle condition measurement sheet 30 is one in which a configuration to output the output of a microphone 34 to the logger 15 is simply added to the evaluation system 10. Accordingly, configurations that act in the same manner as or similarly to the above-mentioned muscle condition measurement sheet 1 and evaluation system 10 use the same numerals and their detailed descriptions are omitted.

As illustrated in FIG. 13, the muscle condition measurement sheet 30 is formed of a flexible print circuit where the pair of stimulating electrodes 32 including the anode 32a and the cathode 32b, the four myoelectric detection electrodes 33a, 33b, 33c, and 33d, the unillustrated lead patterns 6 connected respectively to the myoelectric detection electrodes 33 are printed and formed on the bottom side of the flexible rectangular insulating sheet body 22 made of PET or the like. The microphone 34 serving as the mechanomyography sensor is inserted into a mounting hole 35 drilled between the anode 32a and the cathode 32b of the insulating sheet body 22 and fixed integrally therein. A detection surface 34a of the microphone 34 appears on the bottom surface of the insulating sheet body 22.

It is also considered that when an electrical stimulation signal is applied to the muscle 50 of which level of fatigue is evaluated to innervate the muscle 50, a muscle action potential is evoked in the muscle 50 as described above, and also the muscle 50 expands sideward when the innervated muscle fibers contract to generate a kind of pressure wave. The mechanomyography sensor 34 detects, as muscle sound, mechanical displacement of micro vibration in which the muscle 50 contracts and expands sideward. The data processing device 16 converts it into an analyzable electrical signal. The frequency and amplitude of the muscle sound is considered to have a certain correlation with the state of activity of the muscle 50 as described below. An accelerometer or microphone can be used as the mechanomyography sensor for the purpose of evaluating the state of activity of the muscle 50. In the embodiment, the mechanomyography sensor is attached integrally to the muscle condition measurement sheet 30 to be brought into intimate contact with the body surface of the muscle 50. Accordingly, an accelerometer that performs detection including acceleration caused by body movements during exercise is not suitable; therefore, the microphone 34 is used.

The anode 32a and the cathode 32b of the pair of stimulating electrodes 32 each have a rectangular outline, and appear along both opposing longitudinal sides of the bottom surface of the insulating sheet body 22. Also in the embodiment, an electrical stimulation signal output between the anode 32a and the cathode 32b from the stimulation generation device 12 is equal to or greater than 5 mA. Accordingly, the exposure areas of the anode 32a and the cathode 32b, which are exposed from the bottom surface of the insulating sheet body 22, are respectively set to equal to or greater than 100 mm$^2$ to prevent the electrical stimulation signal from causing pain.

Moreover, as illustrated in FIG. 14, the muscle condition measurement sheet 30 positions itself on the body surface such that its longitudinal direction agrees with the direction of the muscle fibers of the muscle 50 to be evaluated. Accordingly, the interval between the anode 32a and the cathode 32b in the longitudinal direction of the insulating sheet body 22 is shorter than at least the length of the muscle fiber of the muscle 50 to bring both the anode 32a and the cathode 32b into intimate contact with the body surface of the muscle 50 to be evaluated.

The four myoelectric detection electrodes 33a, 33b, 33c, and 33d appear at positions on the four corners of the rectangle parallel to the perimeter of the insulating sheet body 22 between the anode 32a and the cathode 32b on the bottom surface of the insulating sheet body 22. In this manner, the myoelectric detection electrodes 33a, 33b, 33c, and 33d that detect muscle action potentials may be placed between the pair of stimulating electrodes 32a and 32b. Moreover, the propagation speed of the M-wave is set to 3 m/s to 5 m/s, the frequency of the M-wave to equal to or less than 200 Hz, and the interval between the myoelectric detection electrodes 33a and 33b and the myoelectric detection electrodes 33c and 33d, which are spaced in the longitudinal direction of the insulating sheet body 22, to less than at least 15 mm. Consequently, it is configured to be capable of securely detecting the propagation speed of the M-wave based on the difference between an average of the latencies of the myoelectric detection electrodes 33a and 33b and an average of the latencies of the myoelectric detection electrodes 33c and 33d.

As illustrated in FIG. 14, the detection surface 34a of the microphone 34 is formed in a convex surface slightly protruding from the bottom surface of the insulating sheet body 22. Consequently, the detection surface 34a comes into intimate contact with the body surface of the muscle 50 to ensure the detection of muscle sound produced by micro vibration toward the sides of the muscle 50. Moreover, the detection surface 34a appears at the middle position between the anode 32a and the cathode 32b being the pair of stimulating electrodes 32 on the bottom surface of the muscle condition measurement sheet 30. Accordingly, as illustrated, when the anode 32a and the cathode 32b are brought into intimate contact with the body surface on both sides in the direction of the muscle fibers of the muscle 50, the detection surface 34a is brought into intimate contact with the body surface in the middle of the muscle 50 which is in close proximity to the electrical stimulation position, bulges sideward, and has the largest amplitude, and accordingly can detect muscle sound produced in the muscle 50 with high accuracy.

In order to evaluate the level of fatigue of the muscle 50 based on the muscle sound detected by the microphone 34 in the evaluation system, while the muscle 50 is continuously being contracted and expanded, an electrical stimulation signal is applied to the anode 32a and the cathode 32b and also the waveform of the muscle sound detected by the microphone 34 is recorded in the logger 15 at intervals of a fixed elapsed time. The data processing device 16 generates an evoked mechanomyogram MMG representing the waveform of the muscle sound recorded in the logger 15.

When the fatigue of the muscle 50 increases with the progress of the exercise, the sideward spread of the muscle fibers is gradually reduced, and the amplitude is reduced. Accordingly, the fatigue of the muscle 50 can be evaluated based on the amplitude of the muscle sound represented in the evoked mechanomyogram MMG at intervals of the fixed elapsed time.

On the other hand, the propagation speed of the M-wave is detected at intervals of a fixed elapsed time based on the difference between the latencies of the myoelectric detection electrodes 33a and 33b and the myoelectric detection electrodes 33c and 33d between electrical stimulation and the detection of the M-wave and the interval between the myoelectric detection electrodes 33a and 33b and the myoelectric detection electrodes 33c and 33d along the longitudinal direction of the muscle condition measurement sheet 30; accordingly, fatigue of the muscle 50 can also be evaluated based on a reduction in the propagation speed of the M-wave.

Moreover, when the fatigue of the muscle 50 increases, the number of motor units recruited and their firing rates for compensating the contractility of the muscle 50 increase, and the amplitude of the muscle action potential appearing on the evoked electromyogram EMG also increases. Accordingly, the level of fatigue of the muscle 50 can also be evaluated based on a change in the amplitude of the M-wave.

Moreover, muscle stiffness being a measure of stiffness resulting from the muscle 50 becoming tighten with increasing muscle fatigue depends on density as a substance. The resonance frequency of an object depends on the density of the object. Accordingly, muscle stiffness can also be evaluated quantitatively based on the resonance frequency of muscle sound observed by gradually changing the frequency of the electrical stimulation signal. The frequency of muscle sound is equal to or less than 100 Hz that is smaller by one order of magnitude than the frequency of the M-wave. For example, the frequency of the electrical stimulation signal is gradually increased from 1 Hz to 100 Hz. In the data processing device 16, a mechanomyogram signal around the time when the maximum amplitude of the mechanomyogram MMG is obtained is extracted to find the power spectral density of the extracted mechanomyogram signal by an FFT method (Fourier transform). The frequency at the time when the peak value of the power spectral density is obtained is assumed as the resonance frequency.

Furthermore, the type of the muscle 50 to be evaluated, a fast muscle or a slow muscle, can be evaluated based on whether or not the frequency component of the evoked mechanomyogram MMG is in synchronization with the frequency of the electrical stimulation signal. For example, the soleus that is the slow muscle type cannot mechanically follow high-frequency stimulation and accordingly is out of sync with the electrical stimulation signal.

In this manner, various states of activity of the muscle 50 can be objectively evaluated from muscle sound and muscle action potentials generated by the application of electrical stimulation. However, in a case of evaluation by any method, the pair of stimulating electrodes 32 including the anode 32a and the cathode 32b, the four myoelectric detection electrodes 33a, 33b, 33c, and 33d, and the microphone 34 are formed integrally with the insulating sheet body 22 of the muscle condition measurement sheet 30. The pair of stimulating electrodes 32, the four myoelectric detection electrodes 33a, 33b, 33c, and 33d, and the microphone 34 appear on the bottom surface of the muscle condition measurement sheet 30 at fixed intervals between them. Accordingly, the electrical stimulation position and the detection positions that detect muscle action potentials and muscle sound are always fixed. The electrical stimulation position and the detection positions do not move even during exercise. Accordingly, the state of activity of the muscle 50 can be correctly evaluated based on muscle action potentials and muscle sound.

In the above-mentioned embodiments, the adhesive layer adheres the bottom surface of the insulating sheet to the body surface of the muscle 50. However, as long as the insulating sheet can be positioned at a predetermined position on the body surface, positioning can be performed by winding it around the body surface with a band or the like.

Moreover, the intervals between the plurality of myoelectric detection electrodes that is attached integrally to the bottom surface of the insulating sheet are not necessarily required to be equidistant as long as they are known intervals.

Moreover, the configurations of the units of the evaluation system connected to the muscle condition measurement sheet may be wearable, placed in a device that is attached to a body by a band or the like.

Moreover, the reference electrode serves as the cathode of the stimulating electrode, but may be attached to the insulating sheet body separately from the cathode.

Moreover, the propagation speed of the M-wave is detected taking, as latency, the time between the application of an electrical stimulation signal and the detection of the rise of the M-wave at the myoelectric detection electrode. However, as long as any point of time between the start and the end of the M-wave after the application of an electrical stimulation signal can be identified, the period until the point of time may be taken as latency to detect the propagation speed of the M-wave.

The present disclosure is suitable for a muscle condition measurement sheet used in an evaluation system that evaluates the state of activity of a muscle during exercise.

The invention claimed is:

1. A muscle condition measurement sheet used in an evaluation system for positioning a back surface of an insulating sheet of a body surface of a muscle to be measured, the back surface being on a side facing the body surface, applying an electrical stimulation signal to a body surface near the muscle to be measured, and evaluating a state of activity of the muscle based on muscle action potentials appearing on the body surface near the muscle, the muscle condition measurement sheet comprising:
a pair of stimulating electrodes including an anode and a cathode between which an electrical stimulation signal is output;
at least one myoelectric detection electrode configured to detect a muscle action potential evoked by the electrical stimulation signal;
an insulating sheet causing the pair of stimulating electrodes and the at least one myoelectric detection electrode to appear on a back surface thereof such that an interval between the pair of stimulating electrodes and each of the at least one myoelectric detection electrode, which are exposed from the back surface, is shorter than a length of a muscle fiber of the muscle to be measured;
lead patterns wired on the insulating sheet to extend the pair of stimulating electrodes and all the at least one myoelectric detection electrode respectively to external circuits, wherein
the cathode of the pair of stimulating electrodes is placed between the anode of the pair of stimulating electrodes and all the at least one myoelectric detection electrode,
the pair of stimulating electrodes and all the at least one myoelectric detection electrode are brought into intimate contact with a body surface, spaced at predetermined intervals, and
wherein the evaluation system is further for obtaining a propagation speed of the muscle action potential evoked by the electrical stimulation signal, based on latencies of the at least one myoelectric detection electrode in the detection of the muscle action potential, and evaluating the state of activity of the muscle based on the propagation speed.

2. The muscle condition measurement sheet according to claim 1, wherein
a reference electrode having a constant potential appears on the back surface of the insulating sheet, and
muscle action potential of the at least one myoelectric detection electrode is detected based on a difference in potential from the reference electrode when placed in intimate contact with the body surface.

3. The muscle condition measurement sheet according to claim 1, wherein the insulating sheet is a long and slim band-shaped sheet body to be positioned on the body surface along the muscle to be measured,
the pair of stimulating electrodes is caused to appear at one end in a longitudinal direction of the back surface of the sheet body, and
the at least one myoelectric detection electrode is caused to appear respectively at different positions along the longitudinal direction from one end toward the other end of the back surface of the sheet body.

4. The muscle condition measurement sheet according to claim 1, wherein the pair of stimulating electrodes and the at least one myoelectric detection electrode is caused to appear respectively at positions distributed on a flat surface of the back surface of the insulating sheet.

5. The muscle condition measurement sheet according to claim 4, wherein
the pair of stimulating electrodes is caused to appear at one end of the back surface of the insulating sheet, and
the at least one myoelectric detection electrode is caused to appear respectively at positions distributed in a grid pattern on the back surface of the insulating sheet.

6. The muscle condition measurement sheet according to claim 4, wherein
a position where one of the pair of stimulating electrodes, the anode or the cathode, appears on the back surface of the insulating sheet is centered at a center, and the other of the pair of stimulating electrodes is caused to appear in a ring form at a position around the center, and
the at least one myoelectric detection electrode is caused to appear respectively at positions distributed on a plurality of circles being concentric around the center.

7. The muscle condition measurement sheet according to claim 1, wherein
the electrical stimulation signal is equal to or greater than 5 mA, and
an exposure area of at least one of the pair of stimulating electrodes exposed from the back surface of the insulating sheet is equal to or greater than 100 mm$^2$.

8. The muscle condition measurement sheet according to claim 1, wherein the pair of stimulating electrodes is caused to appear on the back surface, protruding from the back surface of the insulating sheet.

9. The muscle condition measurement sheet according to claim 1, wherein an interval between the at least one myoelectric detection electrode appearing on the back surface of the insulating sheet along the muscle to be measured is less than 15 mm.

10. The muscle condition measurement sheet according to claim 1, wherein each lead pattern connected to a corresponding one of the at least one myoelectric detection electrode thereof is formed in a shape with a cross-sectional area thereof increased in proportion to a length of the lead pattern.

11. The muscle condition measurement sheet according to claim 10, wherein a periphery of the lead pattern is surrounded by a ground conductor, spaced with an insulating interval.

12. The muscle condition measurement sheet according to claim 1, further comprising a mechanomyography sensor configured to detect micro vibration of the muscle to be measured when induced by the electrical stimulation signal, wherein
the insulating sheet includes the mechanomyography sensor having a detection surface appearing at a position, which does not interfere with the pair of stimulating electrodes and the at least one myoelectric detection electrode, on the back surface, and the detection surface of the mechanomyography sensor is adapted to be brought into intimate contact with the body surface at a predetermined distance away from the pair of stimulating electrodes.

13. The muscle condition measurement sheet according to claim 12, wherein the pair of stimulating electrodes is caused to appear in a ring form on both sides across the detection surface of the mechanomyography sensor on the back surface of the insulating sheet, and the back surface on the insulating sheet is adapted to be positioned on the body surface in such a manner as to bring the detection surface of the mechanomyography sensor into intimate contact with the body surface having a maximum lateral displacement orthogonal to a muscle fiber direction of the muscle to be measured.

14. The muscle condition measurement sheet according to claim 12, wherein the mechanomyography sensor is a microphone.

15. A muscle condition measurement sheet used in an evaluation system for positioning a back surface of an insulating sheet of a body surface of a muscle to be measured, the back surface being on a side facing the body surface, applying an electrical stimulation signal to a body surface near the muscle to be measured, and evaluating a state of activity of the muscle based on muscle action potentials appearing on the body surface near the muscle, the muscle condition measurement sheet comprising:

a pair of stimulating electrodes including an anode and a cathode between which an electrical stimulation signal is output;

at least two myoelectric detection electrodes configured to detect a muscle action potential evoked by the electrical stimulation signal;

an insulating sheet causing the pair of stimulating electrodes and the at least two myoelectric detection electrodes to appear on a back surface thereof such that an interval between the pair of stimulating electrodes and each of the at least two myoelectric detection electrodes, which are exposed from the back surface, is shorter than a length of a muscle fiber of the muscle to be measured;

lead patterns wired on the insulating sheet to extend the pair of stimulating electrodes and the at least two myoelectric detection electrodes respectively to external circuits, and means for measuring muscle condition based on a propagation speed of an M-wave that is obtained by dividing a distance between the at least two myoelectric detection electrodes by a difference between a latency before detecting the M-wave at one of the at least two myoelectric detection electrodes and a latency before detecting the M-wave at another of the at least two myoelectric detection electrodes, wherein the pair of stimulating electrodes and the at least two myoelectric detection electrodes are brought into intimate contact with a body surface, spaced at predetermined intervals.

16. A muscle condition measurement sheet used in an evaluation system for positioning a back surface of an insulating sheet of a body surface of a muscle to be measured, the back surface being on a side facing the body surface, applying an electrical stimulation signal to a body surface near the muscle to be measured, and evaluating a state of activity of the muscle based on muscle action potentials appearing on the body surface near the muscle, the muscle condition measurement sheet comprising:

a pair of stimulating electrodes including an anode and a cathode between which an electrical stimulation signal is output;

at least one myoelectric detection electrode configured to detect a muscle action potential evoked by the electrical stimulation signal;

an insulating sheet causing the pair of stimulating electrodes and the at least one myoelectric detection electrode to appear on a back surface thereof such that an interval between the pair of stimulating electrodes and each of the at least one myoelectric detection electrode, which are exposed from the back surface, is shorter than a length of a muscle fiber of the muscle to be measured;

lead patterns wired on the insulating sheet to extend the pair of stimulating electrodes and the at least one myoelectric detection electrode respectively to external circuits, and means for measuring muscle condition based on a propagation speed of an M-wave that is obtained by dividing a distance between one of the pair of stimulating electrodes and one of the at least one myoelectric detection electrode by a latency before detecting the M-wave, wherein the pair of stimulating electrodes and the at least one myoelectric detection electrode are brought into intimate contact with a body surface, spaced at predetermined intervals.

* * * * *